US011707209B2

(12) United States Patent
Ran et al.

(10) Patent No.: US 11,707,209 B2
(45) Date of Patent: Jul. 25, 2023

(54) DETECTING METHOD AND POSITIONING ANALYSIS METHOD OF HUMAN FUNCTIONAL JOINT ROTATION CENTER

(71) Applicant: CHINA NATIONAL INSTITUTE OF STANDARDIZATION, Beijing (CN)

(72) Inventors: Linghua Ran, Beijing (CN); Zijian Zhou, Beijing (CN); Hongqi Xu, Beijing (CN); Xin Zhang, Beijing (CN); Chaoyi Zhao, Beijing (CN); Huimin Hu, Beijing (CN); He Zhao, Beijing (CN)

(73) Assignee: CHINA NATIONAL INSTITUTE OF STANDARDIZATION, Beijing (CN)

( * ) Notice: Subject to any disclaimer, the term of this patent is extended or adjusted under 35 U.S.C. 154(b) by 0 days.

(21) Appl. No.: 17/764,544

(22) PCT Filed: Mar. 16, 2021

(86) PCT No.: PCT/CN2021/080984
§ 371 (c)(1),
(2) Date: Mar. 29, 2022

(87) PCT Pub. No.: WO2022/116411
PCT Pub. Date: Jun. 9, 2022

(65) Prior Publication Data
US 2022/0400981 A1 Dec. 22, 2022

(30) Foreign Application Priority Data

Dec. 2, 2020 (CN) .......................... 202011391786.6

(51) Int. Cl.
*A61B 5/11* (2006.01)
*A61B 5/00* (2006.01)

(52) U.S. Cl.
CPC .......... *A61B 5/1122* (2013.01); *A61B 5/1127* (2013.01); *A61B 5/4576* (2013.01)

(58) Field of Classification Search
CPC ... A61B 5/1122; A61B 5/1127; A61B 5/4576; A61B 2505/09; A63B 24/0003
See application file for complete search history.

(56) References Cited

U.S. PATENT DOCUMENTS

2021/0286435 A1* 9/2021 Banerjee ................. G06F 3/017

FOREIGN PATENT DOCUMENTS

| CN | 1748642 A | 3/2006 |
| CN | 1969748 A | 5/2007 |

(Continued)

OTHER PUBLICATIONS

Translation of JP 4332669 (Year: 2009).*

(Continued)

*Primary Examiner* — Devin B Henson
(74) *Attorney, Agent, or Firm* — Bayramoglu Law Offices LLC

(57) ABSTRACT

A detecting method and a positioning analysis method of human functional joint rotation center are provided. The detecting method of human functional joint rotation center includes: step 11: in a continuous motion, a human functional joint rotation center FCR is abstracted as a center of a flexible ball; step 12: at any moment during a test, position coordinates of the center of the ball (i.e. FCR) at the moment are determined according to position coordinates of M1, M2 and M3, and then the motion trajectory of the FCR is obtained in the continuous motion; the positioning analysis method performs positioning analysis of joint positions based on morphological parameters collected by 3D scanning. The detecting method is based on an idea of flexible ball, its operation is simple within a certain error range, and the method performs very well in the continuity of trajectory of joint.

6 Claims, 12 Drawing Sheets

(56) References Cited

FOREIGN PATENT DOCUMENTS

| CN | 102486816 A | 6/2012 |
|---|---|---|
| CN | 107806837 A | 3/2018 |
| CN | 108030496 A | 5/2018 |
| CN | 108324282 A | 7/2018 |
| CN | 109272488 A | 1/2019 |
| CN | 110974241 A | 4/2020 |
| JP | H04294986 A | 10/1992 |
| JP | 4332669 B2 | 9/2009 |
| JP | 2014117409 A | 6/2014 |
| WO | 03096920 A1 | 11/2003 |

OTHER PUBLICATIONS

Hiniduma et al., "New least squares solutions for estimating the average centre of rotation and the axis of rotation", Journal of Biomechanics, vol. 35, 2002, pp. 87-93 (Year: 2002).*

C.G.M. Meskers, et al., In vivo estimation of the glenohumeral joint rotation center from scapular bony landmarks by linear regression, Journal of Biomechanics, 1998, pp. 93-96, vol. 31.

Jinlong Liang, et al., Research progress on the measurement method of hip joint rotation center, Orthopedic Journal of China, 2014, pp. 512-515, vol. 22, No. 6.

H. Bao, et al., On the kinematic modelling and the parameter estimation of the human shoulder, Journal of Biomechanics, 1999, pp. 943-950, vol. 32.

Zhang Jianguo, et al., Application of Double-Coordinate System on Motion Measurement of Human Upper-Limb, Computer Measurement & Control, 2007, pp. 1308-1311, vol. 15, No. 10.

H.E.J. Veeger, The position of the rotation center of the glenohumeral joint, Journal of Biomechanics, 2000, pp. 1711-1715, vol. 33.

Liu Zhen-Yu, et al., Estimation for Rotated Center of Shoulder in Human Upper Limb Dynamic Motion Measurement, Journal of Tianjin University of Science & Technology, 2007, pp. 55-58, vol. 22, No. 1.

* cited by examiner limitation of effect of the second principal component on the joint positions $PC2 = \overline{PC2} - 3 \times \delta$
Any other $PCS = \overline{PCS}$ $PC2 = \overline{PC2} + 3 \times \delta$
Any other $PCS = \overline{PCS}$ analysis of range of effect of the third principal component on the joint positions limitation of effect of the third principal component on the joint positions $PC3 = \overline{PC3} - 3 \times \delta$
Any other $PCS = \overline{PCS}$ $PC3 = \overline{PC3} + 3 \times \delta$
Any other $PCS = \overline{PCS}$ analysis of range of effect of the fourth principal component on the joint positions limitation of effect of the fourth principal component on the joint positions $PC4 = \overline{PC4} - 3 \times \delta$
Any other $PCS = \overline{PCS}$ $PC4 = \overline{PC4} + 3 \times \delta$
Any other $PCS = \overline{PCS}$ analysis of range of effect of the fifth principal component on the joint positions limitation of effect of the fifth principal component on the joint positions analysis of range of effect of the sixth principal component on the joint positions

DETECTING METHOD AND POSITIONING ANALYSIS METHOD OF HUMAN FUNCTIONAL JOINT ROTATION CENTER

CROSS REFERENCE TO THE RELATED APPLICATIONS

This application is the national phase entry of International Application No. PCT/CN2021/080984, filed on Mar. 16, 2021, which is based upon and claims priority to Chinese Patent Application No. 202011391786.6, filed on Dec. 2, 2020, the entire contents of which are incorporated herein by reference.

TECHNICAL FIELD

The present invention relates to the technical field of human body detecting and positioning, in particular to a detecting method and a positioning analysis method of human functional joint rotation center.

BACKGROUND

Motion posture analysis is an important research direction in sport events, especially in background of High-tech Olympics. On the one hand, analysis of athletes' motion posture can screen out better athletes, on the other hand, it can help athletes find out posture defects in motion in time, and help athletes carry out further improvement training, especially for sport events with high requirements for motion posture, such as ice and snow events.

Motion posture analysis needs to be based on a digital dummy. A traditional digital dummy is constructed based on knowledge of human body structure and anatomy, and its posture is single. Therefore, the traditional digital dummy cannot satisfy the posture analysis during motioning. In order to analyze the motion posture of the athlete, it is necessary to detect human functional joint rotation center and perform positioning analysis, however, the existing detecting methods of human functional joint rotation center aim to have higher detection accuracy, but continuity of trajectory of detected functional joint rotation center is not good enough. At present, the positioning analysis methods of human functional joint are based on kinematic parameters, although they can achieve high-precision positioning analysis results, their positioning processes are complicated and take long time.

SUMMARY

In order to solve the above technical problems, the present invention provides a detecting method and a positioning analysis method of human functional joint rotation center. The detecting method is based on an idea of flexible ball, and its operation is simple within a certain error range, the most important thing is that the method performs very well in the continuity of trajectory of joint. The positioning analysis method only needs a short 3D scanning of a human body to obtain positions of the joint rotation centers of a whole body, which makes the positioning analysis of the joint get rid of a complex kinematics analysis, and can estimate the position of the joint more quickly.

A first aspect of the present invention provides a detecting method of human functional joint rotation center, the detecting method includes:

step 11: in a continuous motion, a human functional joint rotation center FCR is abstracted as a center of a flexible ball, and the flexible ball meets constraint conditions:

A. distances between three mark points M1, M2 and M3 on a relevant body section of the FCR are within a specified range, and the three mark points M1, M2 and M3 are points on a spherical surface of the flexible ball;

B. distances between the center of the ball FCR and the points M1, M2, M3 on the ball (namely radii of the ball) are within a specified range rather than an exact value;

C. a motion trajectory of the FCR is continuous;

step 12: at any moment during a test, position coordinates of the center of the ball (i.e. FCR) at the moment are determined according to position coordinates of M1, M2 and M3 on the relevant body section of the FCR, and then in a continuous motion, position information of the center of the ball (i.e. FCR) is determined according to position information of the M1, M2 and M3, and then the motion trajectory of the FCR is obtained in the continuous motion.

Preferably, the human functional joint rotation center FCR refers to at least one of a shoulder joint FCR, an elbow joint FCR, a hip joint FCR and a knee joint FCR.

In any of the above solutions, it is preferred that for the shoulder joint FCR detection, the relevant body section is an upper arm, that is, the mark points M1, M2 and M3 are located on the upper arm; for the elbow joint FCR detection, the relevant body section is a human forearm, that is, the mark points M1, M2 and M3 are located on the forearm; for the hip joint FCR detection, the relevant body section is a human thigh, that is, the mark points M1, M2 and M3 are located on the human thigh; for the knee joint FCR detection, the relevant body section is a human shin, and the mark points M1, M2, and M3 are located on the human shin.

In any of the above solutions, it is preferred that the step 12 includes:

step 121: local coordinate systems are established; the local coordinate systems include a chest coordinate system, a mark point coordinate system, and at least one of an upper arm coordinate system, a forearm coordinate system, a thigh coordinate system and a shin coordinate system;

step 122: position coordinates of the mark points M1, M2 and M3 in an absolute coordinate system are converted to position coordinates in the chest coordinate system;

step 123: a rotation matrix between the local coordinate systems is calculated and the position coordinates of the human functional joint rotation center FCR in the local coordinate system is calculated;

step 124: the position coordinates of the human functional joint rotation center FCR in the local coordinate system are converted to the position coordinates in the chest coordinate system by the rotation matrix, and then converted to the position coordinates in the absolute coordinate system, so as to obtain a detection result of the human functional joint rotation center FCR.

In any of the above solutions, it is preferred that for the shoulder joint FCR detection, the local coordinate system includes the chest coordinate system and the upper arm coordinate system; for the elbow FCR detection, the local coordinate system includes the chest coordinate system, the upper arm coordinate system and the forearm coordinate system; for the hip joint FCR detection, the local coordinate system includes the chest coordinate system and the thigh coordinate system; for the knee joint FCR detection, the local coordinate system includes the chest coordinate system, the thigh coordinate system and the shin coordinate system.

In any of the above solutions, it is preferred that for the shoulder joint FCR detection, a specific process of the step 12 is:

(1) in a positioning motion, the position coordinates of the mark points M1, M2 and M3 in the absolute coordinate system are converted to the position coordinates in the chest coordinate system;

(2) in the chest coordinate system, the coordinates of the shoulder joint FCR are fixed, so in the chest coordinate system a relationship of distance from centers $P_{Ot}^L$ and $P_{Ot+dt}^L$ of a mark point set to the shoulder joint FCR $P_{Jt}$ and $P_{Jt+dt}$ is expressed as:

$$|P_{Jt} - P_{Ot}^L| = |P_{Jt+dt} - P_{Ot+dt}^L| \qquad (1)$$

$$P_{Jt} = P_{Jt+dt} = P_{Ot}^L + R_t^L \tilde{P}_J^L \qquad (2)$$

wherein, $R_t^L$ is the rotation matrix of the upper arm, $\tilde{P}_J^L$ is a constant vector from an origin to the shoulder joint FCR in the mark point coordinate system of the upper arm, $P_{Jt}$ is the coordinates of the shoulder joint FCR in the chest coordinate system at time t, $P_{Jt+dt}$ is the coordinates of the shoulder joint FCR in the chest coordinate system at time t+dt, dt is less than or equal to 1 second;

(3) a linear equation is obtained by combining equation ① and equation ②:

$$A_t \tilde{P}_J^L = B_t \qquad (3)$$

wherein $A_t = 2(P_{Ot}^L - P_{Ot+dt}^L)^T R_t^L$, $B_t = -((P_{Ot}^L)^T P_{Ot}^L - (P_{Ot+dt}^L)^T P_{Ot+dt}^L)$;

in the positioning motion from capture time 0 to time T, an integral of equation ③ is:

$$|A_0 \ldots A_t \ldots A_T|^T \tilde{P}_J^L = |B_0 \ldots B_t \ldots B_T|^T \qquad (4)$$

wherein:

$$A_t = 2 \begin{bmatrix} r_{1xt} - r_{1xt+dt} & r_{1yt} - r_{1yt+dt} & r_{1zt} - r_{1zt+dt} \\ \vdots & \vdots & \vdots \\ r_{nxt} - r_{nxt+dt} & r_{nyt} - r_{nyt+dt} & r_{nzt} - r_{nzt+dt} \end{bmatrix},$$

$$B_t = \begin{bmatrix} r_{1xt}^2 + r_{1yt}^2 + r_{1zt}^2 - r_{1xt+dt}^2 - r_{1yt+dt}^2 - r_{1zt+dt}^2 \\ \vdots \\ r_{nxt}^2 + r_{nyt}^2 + r_{nzt}^2 - r_{nxt+dt}^2 - r_{nyt+dt}^2 - r_{nzt+dt}^2 \end{bmatrix},$$

$r_{1xt}$ represents an X coordinate value of the mark point M1 at time t in the upper arm coordinate system, and meanings of other symbols can be inferred from this, n=3;

(4) according to equation ④, $\tilde{P}_J^L$ is determined by a least square method;

(5) $\tilde{P}_J^L$ is converted to the position coordinates in the chest coordinate system by the rotation matrix, and then converted to the coordinates in the absolute coordinate system, and then the detection result of the shoulder joint FCR is obtained.

A second aspect of the present invention provides a positioning analysis method of human functional joint rotation center, the positioning analysis method includes:

step 21: morphological parameters of human body are obtained by 3D scanning;

step 22: according to a fitting relationship between the morphological parameters of human body and human joints, the human joints are positioned and analyzed;

step 23: positioning analysis results of human joints are compensated.

Preferably, the morphological parameters of human body are obtained by carrying out 3D scanning of natural standing posture, upright posture and sitting posture of human body.

In any of the above solutions, it is preferred that determining the fitting relationship between the morphological parameters of human body and human joints described in the step 22 includes:

step 221: the position coordinates of joints under a standing posture of human body are determined;

step 222: N principal components of the morphological parameters of human body are determined by carrying out principal component analysis of the morphological parameters of human body;

step 223: the N principal components of the morphological parameters of human body are fitted with the position coordinates of joints under the standing posture of human body determined in the step 221 to obtain the fitting relationship:

$$\begin{cases} FCRix = a_{ix1} \cdot PC1 + a_{ix2} \cdot PC2 + \ldots + a_{ixN} \cdot PCN \\ FCRiy = a_{iy1} \cdot PC1 + a_{iy2} \cdot PC2 + \ldots + a_{iyN} \cdot PCN \\ FCRiz = a_{iz1} \cdot PC1 + a_{iz2} \cdot PC2 + \ldots + a_{izN} \cdot PCN \end{cases}$$

wherein, FCRix, FCRiy and FCRiz represent an x coordinate, a y coordinate and a z coordinate of a ith joint respectively, $a_{ix1}, a_{ix2}, \ldots, a_{ixN}, a_{iy1}, a_{iy2}, \ldots, a_{iyN}, a_{iz1}, a_{iz2}, \ldots, a_{izN}$ are fitting coefficients, PC1, PC2, ..., PCN are N principal components of the morphological parameters of human body.

In any of the above solutions, it is preferred that in the step 221, the position coordinates of the shoulder joint, the elbow joint, the hip joint and the knee joint are determined by the mentioned detecting method of human functional joint rotation center.

In any of the above solutions, it is preferred that in the step 221, for joints at limb ends and joints of human trunk, the coordinates of bony landmarks are used to represent the position coordinates of these joints.

In any of the above solutions, it is preferred that in the step 23, compensation of the positioning analysis results of human joints includes translation and rotation.

In any of the above solutions, it is preferred that the translation includes: selecting a standard joint point of the translation; calculating a difference between measured coordinates and the positioning coordinates of the standard joint point to determine a translation amount; translating all positioned joints according to the translation amount.

In any of the above solutions, it is preferred that the rotation includes: selecting a standard joint point of the rotation; calculating an upper limb rotation amount of a wrist joint after translation and the wrist joint before translation relative to a height axis passing through the standard joint point of the rotation; rotating joints on the upper limb after the translation according to the upper limb rotation amount.

In any of the above solutions, it is preferred that the rotation further includes: selecting a standard joint point of the rotation; calculating a lower limb rotation amount of an ankle joint after translation and the ankle joint before translation relative to a height axis passing through the standard joint point of rotation; rotating joints on the lower limb after translation according to the lower limb rotation amount.

The detecting method of human functional joint rotation center is based on the idea of flexible ball, and its operation is simple within a certain error range, the most important thing is that the method performs very well in the continuity of trajectory of joint, and can obtain the motion trajectory of joint rotation center with very good continuity. The positioning analysis method is based on the detecting method. It establishes the fitting relationship between the morphological parameters of human body and a joint position, so that it only needs a short 3D scanning of a human body to obtain positions of the joint rotation centers of a whole body, which makes the positioning analysis of the joint get rid of a complex kinematics analysis, although compared with calculating the joint positions based on kinematic parameters, some calculation accuracy is lost, it can estimate the position of the joint more quickly. The detecting method and positioning analysis method of human functional joint rotation center of the present invention can be used for collecting and analyzing the motion posture of athletes in sport events.

DETAILED DESCRIPTION OF THE EMBODIMENTS

For better understanding of the present invention, detailed description of the invention is provided below with reference to specific embodiments.

In order to better describe the present invention in detail, firstly, some concepts involved in the present invention are briefly introduced.

Detecting of human functional joint rotation center refers to calculating a position of functional rotation center of joint according to kinematic parameters of human body in motion.

Positioning analysis of human functional joint rotation center refers to estimating the position of functional rotation center of joint according to morphological parameters of human body in static.

Embodiment 1

To calculate the position of functional rotation center FCR of joint according to the kinematic parameters of human body in motion, there are two preconditions under ideal conditions: trunk motion can be ignored; skin deformation can be ignored.

Ignoring the trunk motion, it can be considered that the FCR is fixed in a short time, so a distance from a mark point on a relevant body section of the FCR to the FCR is fixed, therefore, the FCR can be abstracted as a center of a ball, and the mark point on the relevant body section can be abstracted as a point on a spherical surface of the ball. A position of the center FCR of the ball can be obtained by detecting positions of at least three mark points attached on the relevant body section in human motion, and treating changed positions of the mark points in a short time as new points on the spherical surface.

A nature that the distance from the mark point on the relevant body section of the FCR to the FCR is fixed is expressed by a formula:

$$|R_t^S - R_{nt}| = |R_{t+dt}^S - R_{nt+dt}|$$

wherein $R_t^S = (r_{xt}^S, r_{yt}^S, r_{zt}^S)^T$ is defined as coordinates of FCR in a measurement coordinate system at time t, $R_{nt} = (r_{nxt}, r_{nyt}, r_{nzt})^T$ represents position of a nth mark point (generally three in total) in the measurement coordinate system at time t. After a very short time dt, a change of position of FCR can be ignored, $R_t^S$ and $R_{t+dt}^S$ is very close, so the position of a transient FCR can be calculated.

In an actual detecting process of human functional joint rotation center, when there is skin deformation, a strict center of ball may not exist, even if the transient FCR can be calculated, a calculation error may be large. Therefore, a detecting method of human functional joint rotation center based on an idea of flexible ball is proposed to reduce an impact of the skin deformation on detection of the FCR.

Figure 1:
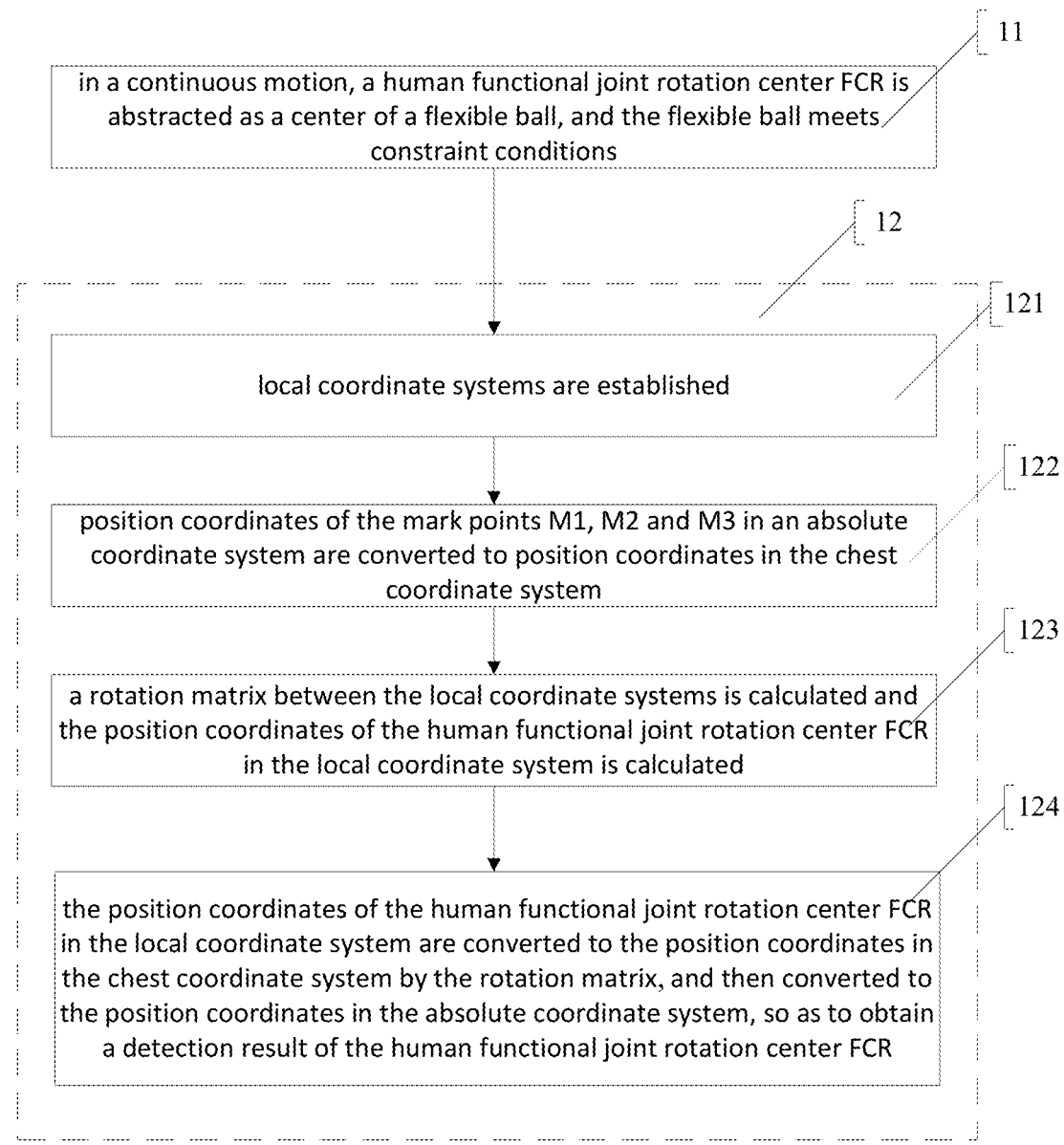
FIG. 1 is a flow diagram of a preferred embodiment of a detecting method of human functional joint rotation center according to the present invention.

As shown in FIG. 1, a detecting method of human functional joint rotation center, includes:

step 11: in a continuous motion, a human functional joint rotation center FCR is abstracted as a center of a flexible ball, and the flexible ball meets constraint conditions:

A. distances between three mark points M1, M2 and M3 on a relevant body section of the FCR are within a specified range, and the three mark points M1, M2 and M3 are points on a spherical surface of the flexible ball;

B. distances between the center of the ball FCR and the points M1, M2, M3 on the ball (namely radii of the ball) are within a specified range rather than an exact value;

C. a motion trajectory of the FCR is continuous;

step 12: at any moment during a test, position coordinates of the center of the ball (i.e. FCR) at the moment are determined according to position coordinates of M1, M2 and M3 on the relevant body section of the FCR, and then in a continuous motion, position information of the center of the ball (i.e. FCR) is determined according to position information of the M1, M2 and M3, and then the motion trajectory of the FCR is obtained in the continuous motion.

In this embodiment, the human functional joint rotation center FCR refers to at least one of a shoulder joint FCR, an elbow joint FCR, a hip joint FCR and a knee joint FCR. For the shoulder joint FCR detection, the relevant body section is an upper arm, that is, the mark points M1, M2 and M3 are located on the upper arm; for the elbow joint FCR detection, the relevant body section is a human forearm, that is, the mark points M1, M2 and M3 are located on the forearm; for the hip joint FCR detection, the relevant body section is a human thigh, that is, the mark points M1, M2 and M3 are located on the human thigh; for the knee joint FCR detection, the relevant body section is a human shin, and the mark points M1, M2, and M3 are located on the human shin.

The step 12 includes:

step 121: local coordinate systems are established; the local coordinate systems include a chest coordinate system, a mark point coordinate system, and at least one of an upper arm coordinate system, a forearm coordinate system, a thigh coordinate system and a shin coordinate system;

step 122: position coordinates of the mark points M1, M2 and M3 in an absolute coordinate system are converted to position coordinates in the chest coordinate system;

step 123: a rotation matrix between the local coordinate systems is calculated and the position coordinates of the human functional joint rotation center FCR in the local coordinate system is calculated;

step 124: the position coordinates of the human functional joint rotation center FCR in the local coordinate system are converted to the position coordinates in the chest coordinate system by the rotation matrix, and then converted to the position coordinates in the absolute coordinate system, so as to obtain a detection result of the human functional joint rotation center FCR.

In this embodiment, for the shoulder joint FCR detection, the local coordinate system includes the chest coordinate system and the upper arm coordinate system; for the elbow FCR detection, the local coordinate system includes the chest coordinate system, the upper arm coordinate system and the forearm coordinate system; for the hip joint FCR detection, the local coordinate system includes the chest coordinate system and the thigh coordinate system; for the knee joint FCR detection, the local coordinate system includes the chest coordinate system, the thigh coordinate system and the shin coordinate system.

In this embodiment, taking the shoulder FCR detection as an example, step 12 is described in detail, step 12 of the elbow joint FCR detection, the hip joint FCR detection and the knee joint FCR detection can refer to the step 12 of the shoulder joint FCR detection.

For the shoulder joint FCR detection, a specific process of the step 12 is:

(1) in a positioning motion, the position coordinates of the mark points M1, M2 and M3 in the absolute coordinate system are converted to the position coordinates in the chest coordinate system;

(2) in the chest coordinate system, the coordinates of the shoulder joint FCR are fixed, so in the chest coordinate system a relationship of distance from centers $P_{Ot}^{L}$ and $P_{Ot+dt}^{L}$ of a mark point set to the shoulder joint FCR $P_{Jt}$ and $P_{Jt+dt}$ is expressed as:

$$|P_{Jt}-P_{Ot}^{L}|=|P_{Jt+dt}-P_{Ot+dt}^{L}| \qquad (1)$$

$$P_{Jt}=P_{Jt+dt}=P_{Ot}^{L}+R_{t}^{L}\tilde{P}_{J}^{L} \qquad (2)$$

wherein, $R_{t}^{L}$ is the rotation matrix of the upper arm, $\tilde{P}_{J}^{L}$ is a constant vector from an origin to the shoulder joint FCR in the mark point coordinate system of the upper arm, $P_{Jt}$ is the coordinates of the shoulder joint FCR in the chest coordinate system at time t, $P_{Jt+dt}$ is the coordinates of the shoulder joint FCR in the chest coordinate system at time t+dt, dt is less than or equal to 1 second;

(3) a linear equation is obtained by combining equation ① and equation ②:

$$A_t\tilde{P}_J^L=B_t \qquad (3)$$

wherein $A_t=2(P_{Ot}^{L}-P_{Ot+dt}^{L})^T R_t^L$, $B_t=-((P_{Ot}^{L})^T P_{Ot}^{L}-(P_{Ot+dt}^{L})^T P_{Ot+dt}^{L})$;

in the positioning motion from capture time 0 to time T, an integral of equation ③ is:

$$|A_0 \ldots A_t \ldots A_T|^T \tilde{P}_J^L = |B_0 \ldots B_t \ldots B_T|^T \qquad (4)$$

wherein:

$$A_t = 2\begin{bmatrix} r_{1xt}-r_{1xt+dt} & r_{1yt}-r_{1yt+dt} & r_{1zt}-r_{1zt+dt} \\ \vdots & \vdots & \vdots \\ r_{nxt}-r_{nxt+dt} & r_{nyt}-r_{nyt+dt} & r_{nzt}-r_{nzt+dt} \end{bmatrix},$$

$$B_t = \begin{bmatrix} r_{1xt}^2+r_{1yt}^2+r_{1zt}^2-r_{1xt+dt}^2-r_{1yt+dt}^2-r_{1zt+dt}^2 \\ \vdots \\ r_{nxt}^2+r_{nyt}^2+r_{nzt}^2-r_{nxt+dt}^2-r_{nyt+dt}^2-r_{nzt+dt}^2 \end{bmatrix},$$

$r_{1xt}$ represents an X coordinate value of the mark point M1 at time t in the upper arm coordinate system, and meanings of other symbols can be inferred from this, n=3;

(4) according to equation ④, is determined by a least square method;

(5) $\tilde{P}_J^L$, is converted to the position coordinates in the chest coordinate system by the rotation matrix, and then converted to the coordinates in the absolute coordinate system, and then the detection result of the shoulder joint FCR is obtained.

Directions of three coordinate axes of the chest coordinate system are the same as that of the absolute coordinate system, and an origin position thereof coincides with a position of a suprasternale. A purpose of establishing the chest coordinate system is to offset influences that a trunk displacement causes an upper arm translation during human walking. In the chest coordinate system, a trajectory of upper arm of human is mainly rotation.

An origin of the upper arm coordinate system is at a position of an acromion point, and initial directions of three coordinate axes of the upper arm coordinate system are the same as that of the absolute coordinate system. According to three vectors respectively pointing to the three mark points on the upper arm with the acromion point as the starting point, a rotation amount of the coordinate system before and after dt, that is, the rotation matrix is obtained. According to the rotation matrix at each moment, the directions of three coordinate axes of the upper arm coordinate system are calculated iteratively.

For the mark point coordinate system, since the directions of three coordinate axes of the upper arm coordinate system are not used in the actual detecting process, and only the rotation amount of the three vectors in the upper arm coordinate system is concerned, therefore, the mark point coordinate system is defined as a non-standard coordinate system with an origin at the position of the acromion point and the directions of the three vectors as directions of axes.

The detecting process of the hip joint FCR is similar to that of the shoulder joint FCR.

The detecting process of the elbow joint FCR is slightly different from that of the shoulder joint FCR. Because the elbow joint connects the upper arm and the forearm, in the absolute coordinate system or the chest coordinate system, the elbow joint is mainly affected by a movement of the upper arm, therefore, calculation of the functional rotation center of the elbow joint cannot be directly converted from the chest coordinate system to the forearm coordinate system like that of the functional rotation center of the shoulder joint, but needs to be converted from the chest coordinate system to the upper arm coordinate system first, after offsetting influences of upper arm rotation, the functional rotation center of the elbow joint is calculated according to a relationship between the forearm coordinate system and the upper arm coordinate system. A specific method is: after calculating the rotation matrix from the chest coordinate system to the upper arm coordinate system, make the forearm coordinate system rotate the same amount according to the rotation matrix, and then calculate according to the upper arm coordinate system and the rotated forearm coordinate system.

The detecting process of the knee joint FCR is similar to that of the elbow joint FCR.

Embodiment 2

Figure 2:
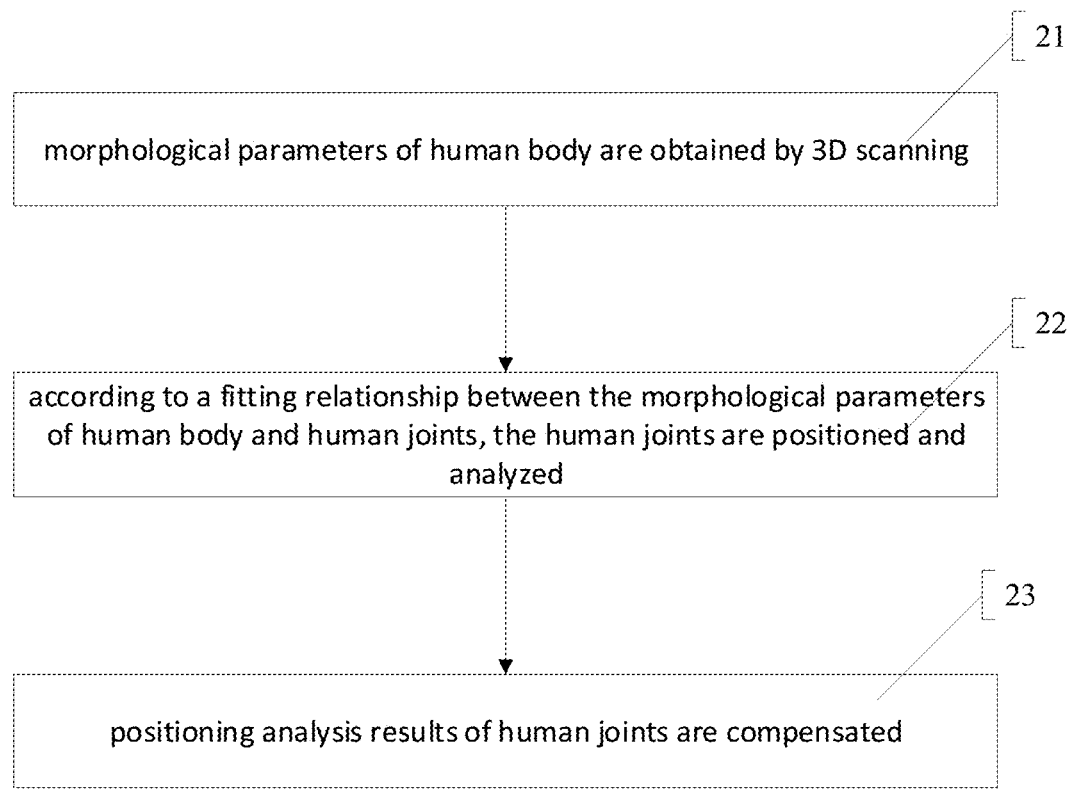
FIG. 2 is a flow diagram of a preferred embodiment of a positioning analysis method of human functional joint rotation center according to the present invention.

As shown in FIG. 2, a positioning analysis method of human functional joint rotation center includes:

step 21: morphological parameters of human body are obtained by 3D scanning;

step 22: according to a fitting relationship between the morphological parameters of human body and human joints, the human joints are positioned and analyzed;

step 23: positioning analysis results of human joint positioning analysis.

Figure 3:
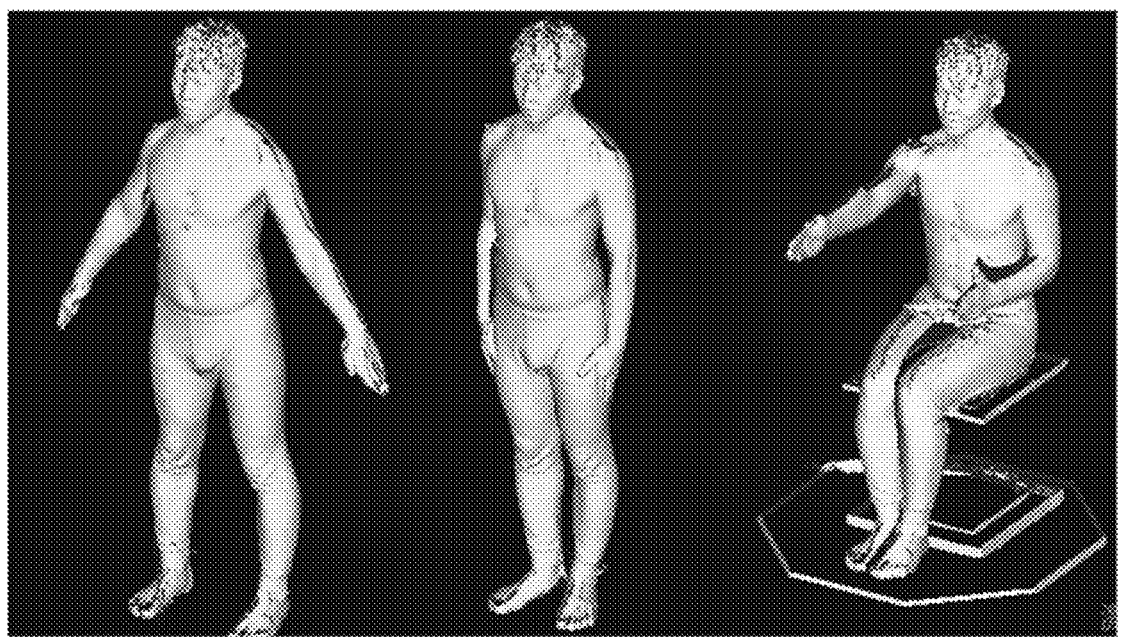
FIG. 3 is a posture diagram of 3D scanning of the embodiment shown in FIG. 2 of the positioning analysis method of human functional joint rotation center according to the present invention.

As shown in FIG. 3, in the step 21, the morphological parameters of human body are obtained by carrying out 3D scanning of natural standing posture (the leftmost posture in the figure), upright posture (the middle posture in the figure) and sitting posture (the rightmost posture in the figure) of human body. In the natural standing posture, human feet are shoulder-width apart, and hands are open at the same time, because human trunk is not close to arms and the legs do not interfere with each other, general girth parameters and width parameters are measured in this posture. In the upright posture, human arms are close to the trunk, legs are close together, and heels of both feet are close, in this posture, human bones are straight and upward, which is very suitable for measuring height parameters. By adjusting a height of a lift chair, in the sitting posture, human thighs are parallel to ground, a right arm is extended horizontally forward, a left upper arm is vertically downward, and a left forearm is horizontally forward.

In the step 22, a determination process of the fitting relationship between the morphological parameters of human body and human joints includes:

step 221: the position coordinates of joints under a standing posture of human body are determined;

step 222: N principal components of the morphological parameters of human body are determined by carrying out principal component analysis of the morphological parameters of human body;

step 223: the N principal components of the morphological parameters of human body are fitted with the position coordinates of joints under the standing posture of human body determined in the step 221 to obtain the fitting relationship:

$$\begin{cases} FCRix = a_{ix1} \cdot PC1 + a_{ix2} \cdot PC2 + \ldots + a_{ixN} \cdot PCN \\ FCRiy = a_{iy1} \cdot PC1 + a_{iy2} \cdot PC2 + \ldots + a_{iyN} \cdot PCN \\ FCRiz = a_{iz1} \cdot PC1 + a_{iz2} \cdot PC2 + \ldots + a_{izN} \cdot PCN \end{cases}$$

wherein, $FCRix$, $FCRiy$ and $FCRiz$ represent an x coordinate, a y coordinate and a z coordinate of a ith joint respectively, $a_{ix1}$, $a_{ix2}$, ..., $a_{ixN}$, $a_{iy1}$, $a_{iy2}$, ..., $a_{iyN}$, $a_{iz1}$, $a_{iz2}$, ..., $a_{izN}$ are fitting coefficients, $PC1$, $PC2$, ..., $PCN$ are N principal components of the morphological parameters of human body.

In the step 221, the position coordinates of the shoulder joint, the elbow joint, the hip joint and the knee joint are determined by the mentioned detecting method of human functional joint rotation center in the embodiment 1. The position coordinates of other joints can be determined according to needs of positioning analysis, such as joints at limb ends and joints of human trunk, so as to analyze and estimate the posture of the whole human body. For the joints at limb ends and the joints of human trunk, the coordinates of bony landmarks are used to represent the position coordinates of these joints.

In the step 23, compensation of the results of positioning and analysis of human joints includes translation and rotation.

The translation includes: selecting a standard joint point of the translation; calculating a difference between measured coordinates and the positioning coordinates of the standard joint point to determine a translation amount; translating all positioned joints according to the translation amount.

The rotation includes: selecting a standard joint point of the rotation; calculating an upper limb rotation amount of a wrist joint after translation and the wrist joint before translation relative to a height axis passing through the standard joint point of the rotation; rotating joints on the upper limb after the translation according to the upper limb rotation amount. The rotation further includes: selecting a standard joint point of the rotation; calculating a lower limb rotation amount of an ankle joint after translation and the ankle joint before translation relative to a height axis passing through the standard joint point of rotation; rotating joints on the lower limb after translation according to the lower limb rotation amount.

Embodiment 3

In order to verify the effectiveness and accuracy of the positioning analysis method of human functional joints rotation center, experiments are carried out.

Figure 4:
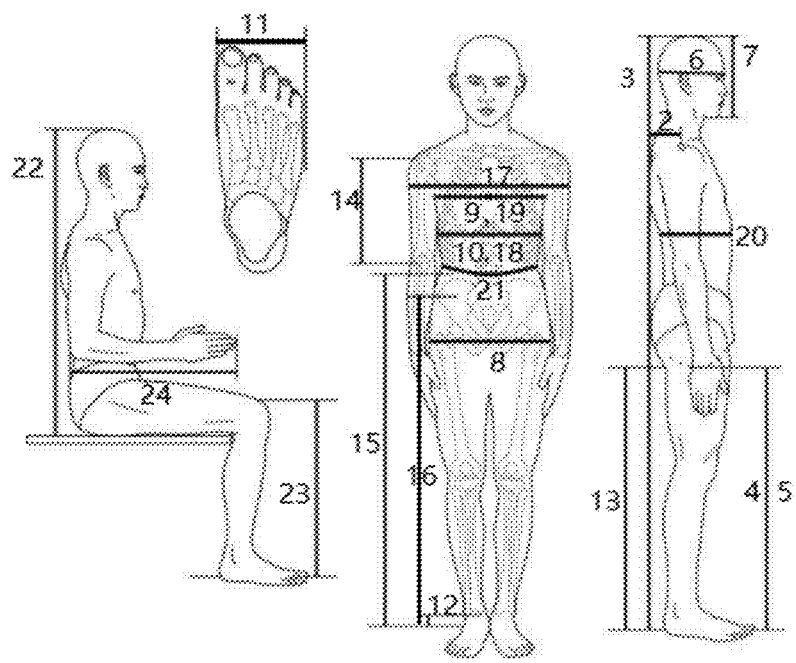
FIG. 4 is a schematic diagram of morphological parameters of another embodiment of the positioning analysis method of human functional joint rotation center according to the present invention.

During the experiment, the morphological parameters of 30 male subjects are collected through 3D scanning, and 24 morphological parameters are collected for each subject, the schematic diagram of each morphological parameter is shown in FIG. 4, and details of the morphological parameters of 30 subjects are shown in Table 1.

TABLE 1 the morphological parameters of 30 subjects

| | morphological parameter (mm or kg) | average | maximum | minimum | variance |
|---|---|---|---|---|---|
| 1 | weight | 70.23 | 100 | 47.4 | 13.21 |
| 2 | distance to wall | 106.13 | 190 | 70 | 22.05 |
| 3 | height | 1689.40 | 1811 | 1601 | 46.96 |
| 4 | crotch height 1 | 713.97 | 823 | 631 | 39.88 |

TABLE 1-continued the morphological parameters of 30 subjects

| | morphological parameter (mm or kg) | average | maximum | minimum | variance |
|---|---|---|---|---|---|
| 5 | crotch height 2 | 736.60 | 849 | 645 | 39.99 |
| 6 | head length | 181.93 | 201 | 116 | 14.64 |
| 7 | total head height | 234.97 | 262 | 212 | 12.47 |
| 8 | hip breadth | 335.57 | 375 | 300 | 20.22 |
| 9 | chest girth | 910.77 | 1160 | 775 | 92.06 |
| 10 | lower chest circumference | 883.07 | 1018 | 732 | 81.33 |
| 11 | foot breadth | 40.93 | 51 | 31 | 5.81 |
| 12 | medial malleolus height | 72.53 | 83 | 60 | 5.33 |
| 13 | hip height (distance from hip to ground) | 787.73 | 899 | 731 | 38.86 |
| 14 | right upper arm length | 318.17 | 341 | 285 | 13.89 |
| 15 | waist height (distance from midpoint of smallest rib and iliocristale to ground) | 1017.20 | 1116 | 965 | 35.95 |
| 16 | hip height (crista iliaca height) | 979.77 | 1077 | 922 | 36.70 |
| 17 | shoulder width (width between two acromion points) | 391.30 | 433 | 366 | 19.05 |
| 18 | chest width corresponding to a height of a lower chest point chest thickness (chest width | 310.90 | 366 | 259 | 26.09 |
| 19 | corresponding to a height of a midpoint of the chest) | 221.30 | 259 | 186 | 21.42 |
| 20 | chest depth (a thickness at the lower chest point) | 232.33 | 292 | 164 | 29.85 |
| 21 | minimum abdominal circumference (girth at the lowest rib) | 849.60 | 1050 | 638 | 108.88 |
| 22 | sitting height | 917.07 | 969 | 861 | 24.73 |
| 23 | knee height, sitting | 500.40 | 549 | 460 | 21.61 |
| 24 | distance form forearm to fingertip | 453.53 | 482 | 428 | 14.84 |

Figure 5:
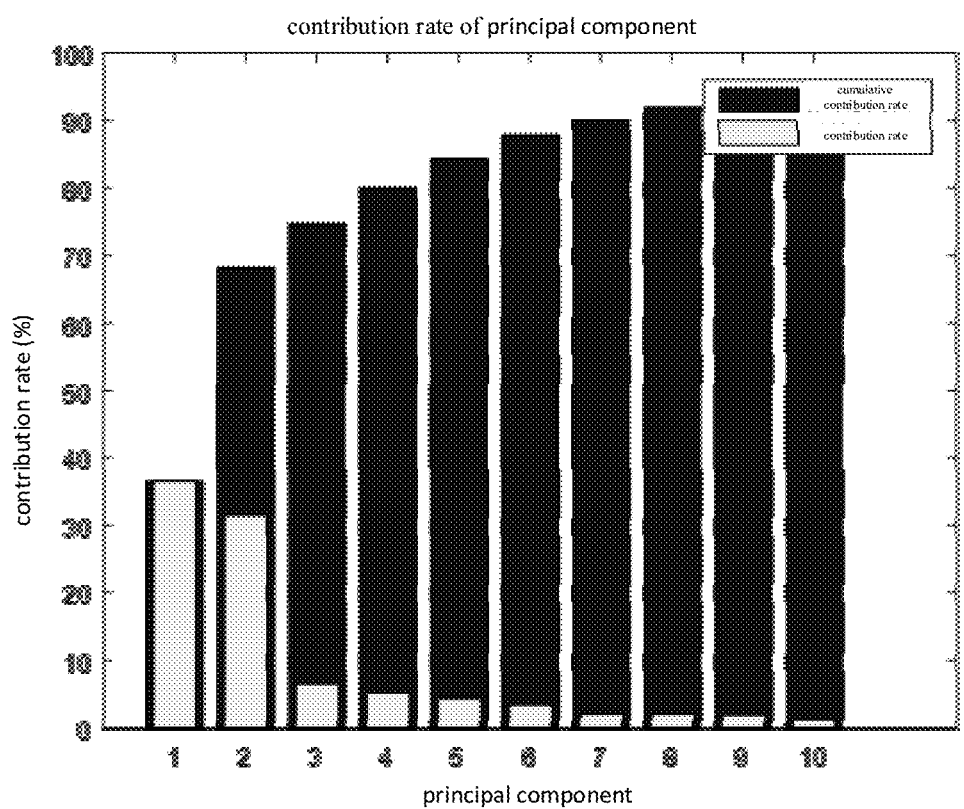
FIG. 5 is a histogram of contribution of principal components of morphological parameters in the embodiment shown in FIG. 4 of the positioning analysis method of human functional joint rotation center according to the present invention.

The morphological parameters obtained by 3D scanning are analyzed by principal component analysis. Before the principal component analysis is carried out, a KMO test statistics and a Bartlett P value should be calculated to verify that the morphological parameters collected by 3D scanning can be analyzed by the principal component analysis. After calculation, KMO value is 0.64 and P value is 0.000, indicating that the collected morphological parameters can be analyzed by the principal component analysis. After principal component analysis, contribution rates of the first 10 principal components of the morphological parameters are shown in FIG. 5, and values of the contribution rates of the first 8 principal components of the morphological parameters are shown in Table 2.

TABLE 2 the contribution rates of the principal components of morphological parameters (the first 8)

| characteristic value | difference | contribution rate(%) | cumulative contribution rate(%) |
|---|---|---|---|
| 8.7988095 | 1.2094706 | 36.6617062 | 36.6617062 |
| 7.5893388 | 6.0191402 | 31.6222451 | 68.2839513 |
| 1.5701986 | 0.3091772 | 6.5424943 | 74.8264456 |
| 1.2610214 | 0.1936826 | 5.2542558 | 80.0807015 |
| 1.0673388 | 0.2282187 | 4.4472451 | 84.5279466 |
| 0.8391202 | 0.3341105 | 3.4963340 | 88.0242806 |
| 0.5050097 | 0.0064812 | 2.1042070 | 90.1284876 |
| 0.4985285 | 0.0339277 | 2.0772020 | 92.2056896 |

It can be seen that the cumulative contribution rate of the first 6 principal components is over 85%, so 6 principal components are selected in this embodiment. In order to find out a corresponding relationship between factors and the morphological parameters, a factor analysis is carried out, and a maximum variance rotation method is used for rotation. The results of the factor analysis are shown in Table 3. It can be seen from the table 3 that corresponding commonality values of morphological parameters are bigger than 0.4, indicating that a correlation between each morphological parameter and factor is strong, and the factors can effectively extract most of information of the morphological parameters.

TABLE 3 factor load coefficient table after rotation

| title | factor 1 | factor 2 | factor 3 | factor 4 | factor 5 | factor 6 | commonality |
|---|---|---|---|---|---|---|---|
| 1. weight | 0.96 | 0.016 | −0.039 | 0.189 | 0.083 | 0.015 | 0.966 |
| 2. distance to wall | 0.579 | −0.03 | −0.687 | −0.137 | 0.23 | 0.067 | 0.884 |
| 3. height | −0.022 | 0.936 | 0.022 | 0.259 | 0.018 | 0.143 | 0.965 |
| 4. crotch height 1 | −0.265 | 0.889 | 0.087 | −0.195 | 0.078 | −0.006 | 0.913 |
| 5. crotch height 2 | −0.188 | 0.896 | −0.005 | −0.231 | 0.051 | 0.066 | 0.899 |
| 6. head length | 0.002 | 0.149 | 0.92 | −0.173 | 0.117 | 0.047 | 0.915 |
| 7. total head height | 0.296 | 0.199 | 0.043 | 0.279 | 0.778 | 0.116 | 0.825 |
| 8. hip breadth | 0.845 | 0.095 | 0.097 | 0.371 | 0.034 | −0.049 | 0.874 |
| 9. chest girth | 0.964 | −0.111 | −0.039 | 0.056 | 0.005 | 0.038 | 0.947 |
| 10. lower chest circumference | 0.948 | −0.097 | −0.104 | 0.091 | 0.12 | 0.016 | 0.942 |
| 11. foot breadth | −0.691 | −0.119 | 0.06 | 0.008 | −0.46 | 0.113 | 0.719 |
| 12. medial malleolus height | 0.292 | 0.198 | −0.173 | 0.724 | 0.288 | −0.015 | 0.762 |
| 13. hip height (distance from hip to ground) | −0.069 | 0.861 | 0.196 | −0.11 | 0.029 | −0.081 | 0.805 |

TABLE 3-continued factor load coefficient table after rotation

| title | factor 1 | factor 2 | factor 3 | factor 4 | factor 5 | factor 6 | commonality |
|---|---|---|---|---|---|---|---|
| 14. right upper arm length | 0.257 | 0.558 | 0.03 | −0.06 | −0.022 | −0.661 | 0.82 |
| 15. waist height (distance from midpoint of smallest rib and iliocristale to ground) | −0.082 | 0.948 | 0.05 | 0.196 | 0.045 | −0.118 | 0.962 |
| 16. hip height (crista iliaca height) | −0.153 | 0.926 | 0.091 | 0.221 | 0.041 | −0.174 | 0.97 |
| 17. shoulder width (width between two acromion points) | 0.579 | 0.31 | 0.191 | −0.217 | 0.193 | 0.571 | 0.879 |
| 18. chest width corresponding to a height of a lower chest point | 0.897 | −0.035 | 0.095 | 0.244 | 0.11 | −0.034 | 0.888 |
| 19. chest thickness (chest width corresponding to a height of a midpoint of the chest) | 0.851 | −0.031 | −0.205 | −0.315 | 0.123 | 0.027 | 0.882 |
| 20. chest depth (a thickness at the lower chest point) | 0.927 | −0.161 | −0.105 | −0.128 | 0.021 | 0.028 | 0.914 |
| 21. minimum abdominal circumference (girth at the lowest rib) | 0.944 | −0.168 | −0.078 | 0.058 | 0.046 | −0.045 | 0.933 |
| 22. sitting height | −0.008 | 0.699 | −0.142 | 0.363 | −0.076 | 0.4 | 0.807 |
| 23. knee height, sitting | 0.218 | 0.863 | −0.075 | 0.186 | 0.094 | 0.017 | 0.841 |
| 24. distance form forearm to fingertip | 0.139 | 0.748 | 0.065 | −0.119 | 0.454 | −0.108 | 0.815 |

The corresponding relationship between the factors and the morphological parameters is analyzed. After analysis, it is considered that there is a corresponding relationship between the morphological parameters and the factors when an absolute value of the factor load coefficient is bigger than 0.4. Therefore, according to a relationship equation between the factors and the morphological parameters, values of the factors are calculated, that is, a sum of products of feature vector elements and each morphological parameter of the subject respectively, and terms with the absolute value of the factor load coefficient bigger than 0.4 in the components are found out, a regression analysis between them are carried out. If a $R^2$ value is too small after adjustments of statistical parameters, the terms whose product of feature vector elements and corresponding morphological parameters is less than an average value should be eliminated for adjustment. Analysis results are shown in Table 4.

TABLE 4 regression analysis of the morphological parameters and their s principal component

| | adjR² | morphological parameter | +/− |
|---|---|---|---|
| the first principal component | 0.9847 | weight | + |
| | | distance to wall | + |
| | | hip breadth | − |
| | | chest girth | + |
| | | foot breadth | + |
| | | lower chest circumference | − |
| | | shoulder width (width between two acromion points) | − |
| | | chest width corresponding to a height of a lower chest point | + |
| | | chest thickness (chest width corresponding to a height of a midpoint of the chest) | − |
| | | chest depth (a thickness at the lower chest point) | + |
| | | minimum abdominal circumference (girth at the lowest rib) | + |

TABLE 4-continued regression analysis of the morphological parameters and their s principal component

| | adjR² | morphological parameter | +/− |
|---|---|---|---|
| the second principal component | 0.9947 | height | + |
| | | crotch height 1 | + |
| | | crotch height 2 | + |
| | | hip height (distance from hip to ground) | + |
| | | right upper arm length | + |
| | | waist height (distance from midpoint of smallest rib and iliocristale to ground) | − |
| | | hip height (crista iliaca height) | + |
| | | sitting height | + |
| | | knee height, sitting | + |
| | | distance form forearm to fingertip | + |
| the third principal component | 0.8134 | distance to wall | − |
| | | head length | + |
| | | medial malleolus height | − |
| | | hip height (distance from hip to ground) | − |
| | | shoulder width (width between two acromion points) | + |
| | | corresponding to a height of a midpoint of the chest) | + |
| the fourth principal component | 0.6742 | height | − |
| | | crotch height 2 | + |
| | | total head height | − |
| | | hip breadth | − |
| | | medial malleolus height | + |
| | | chest thickness (chest width corresponding to a height of a midpoint of the chest) | − |
| | | chest depth (a thickness at the lower chest point) | + |
| | | sitting height | − |
| the fifth principal component | 0.9228 | height | − |
| | | crotch height 2 | − |
| | | right upper arm length | + |
| | | waist height (distance from midpoint of smallest rib and iliocristale to ground) | − |
| | | hip height | + |
| | | shoulder width (width between two acromion points) | − |

TABLE 4-continued regression analysis of the morphological parameters and their s principal component

| | adjR² | morphological parameter | +/− |
|---|---|---|---|
| | | minimum abdominal circumference (girth at the lowest rib) | + |
| | | sitting height | − |
| the sixth principal component | 0.9701 | height | − |
| | | total head height | + |
| | | chest girth | − |
| | | minimum abdominal circumference (girth at the lowest rib) | − |
| | | sitting height | − |
| | | distance form forearm to fingertip | + |

In this embodiment, the position coordinates of 22 joints under the standing posture of the human body are determined. The 22 joints include the shoulder joints, the elbow joints, the hip joints and the knee joints, and the position coordinates of the shoulder joints, the elbow joints, the hip joints and the knee joints are calculated by the detecting method of human functional joint rotation center. The position coordinates of the other joints are represented by the coordinates of bone landmarks.

There are two kinds of joints in human body that can be represented by bone landmarks, one is the joints at limb ends, such as hands and feet, this kind of joints are lack of motion information but can be described easily; the other is the joints of the human trunk, this kind of joints are complex but simple movements (such as walking) cause less trunk movement or deformation, so they can also be represented by bone landmarks. The first kind of joints includes hand joint and foot joint. The hand joint is represented by a midpoint of the second finger and the fifth finger which is on a midline of a hand length, and the foot joint is represented by a midpoint of the first toe and the fourth toe which is on a midline of a foot length. The second kind of joints are mainly on the head and the trunk, the points used to represent the joints on the head include a glabella and a middle point of tragions, the point used to represent the joint at neck is cervicale, and the points used to represent the joints on the trunk include thoracic vertebrae point, a center of a left iliospinale anterius, a right iliospinale anterius, a left iliospinale posterius and a right iliospinale posterius, a middle point of a connecting line of the left greater trochanter and the right greater trochanter. This kind of joints corresponds to forehead (end of head), head-neck joint, neck-chest joint, chest-abdomen joint, abdomen-pelvic joint and pelvic center respectively. In addition, rotation angles of wrist joint and ankle joint are small during a gait measurement, so the wrist joint and the ankle joint are represented by a middle point of styloid process and styloid process of ulna and a middle point of medial and lateral malleolus respectively.

After determining the positions of the 22 joints under the standing posture of human body, a total of 66 coordinate values are obtained because of the position of each joint described by 3D coordinates. Each coordinate value is linearly fitted with the principal components of morphological parameters, and the fitting relationship between human morphological parameters and human joint position coordinates is obtained. Through the fitting relationship, the positioning analysis of human joint can be carried out according to the morphological parameters to estimate the joint rotation center.

Figure 6A:
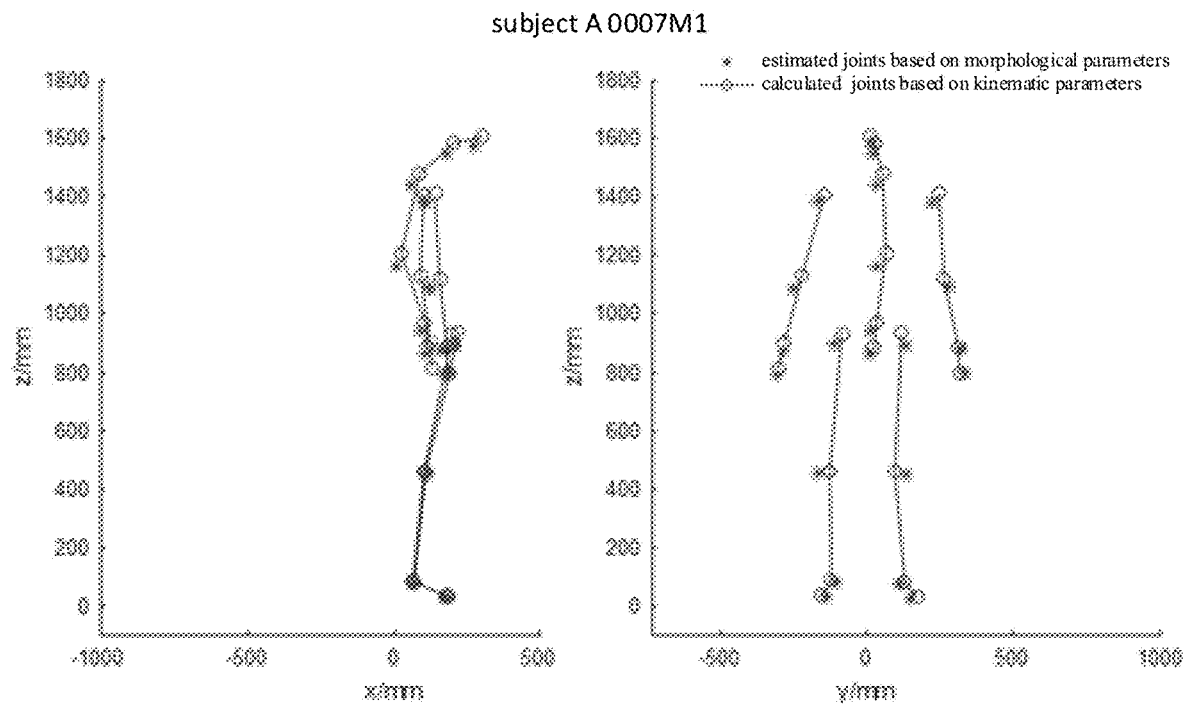
FIG. 6A shows positioning analysis results of subject 7 before compensation in the embodiment shown in FIG. 4 of the positioning analysis method of human functional joint rotation center according to the present invention.
Figure 6B:
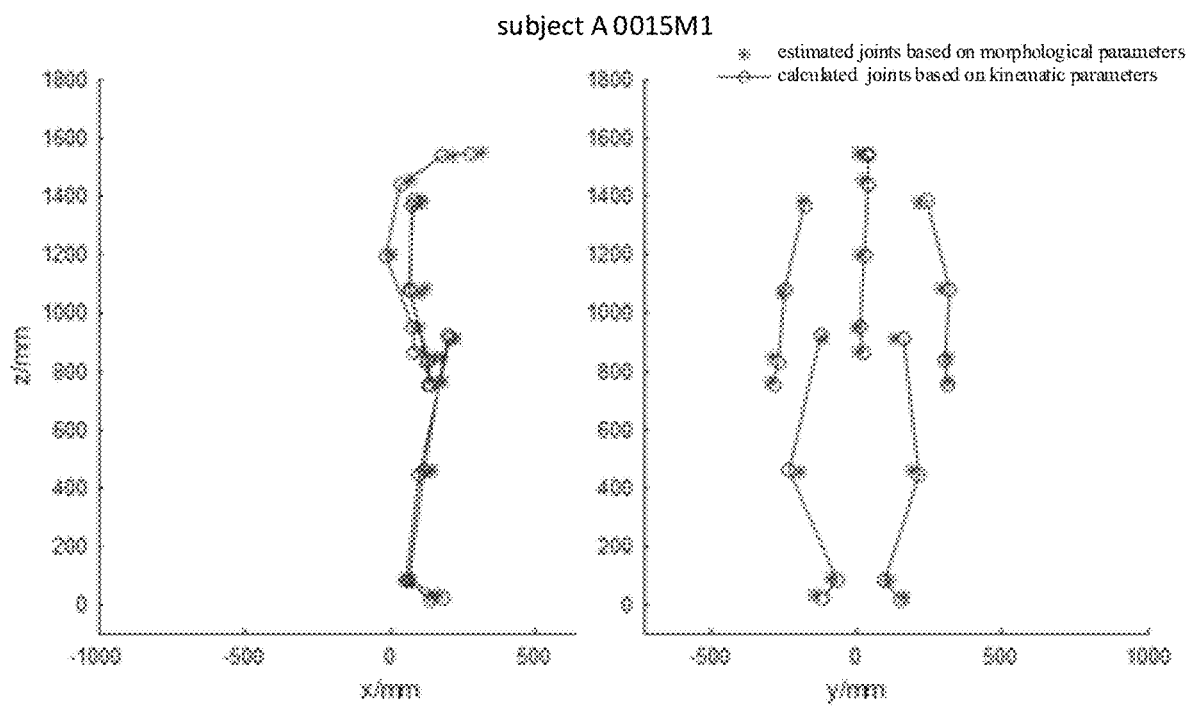
FIG. 6B shows positioning analysis results of subject 15 before compensation in the embodiment shown in FIG. 4 of the positioning analysis method of human functional joint rotation center according to the present invention.
Figure 6C:
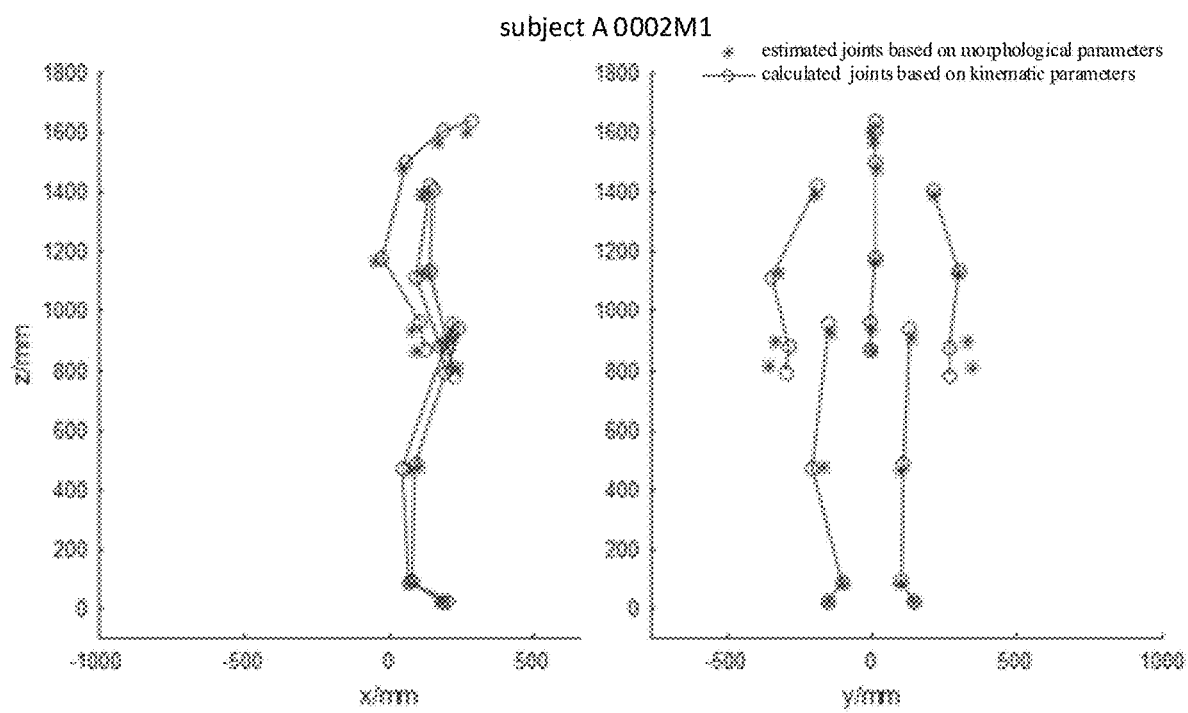
FIG. 6C shows positioning analysis results of subject 2 before compensation in the embodiment shown in FIG. 4 of the positioning analysis method of human functional joint rotation center according to the present invention.

According to the fitting relationship between human morphological parameters and human joint position coordinates, the positioning analysis of human joint is carried out. FIGS. 6A-6C show schematic diagrams of positioning the joints of subject 7, subject 15 and subject 2, and comparing the positioning results with the joint positions calculated according to the kinematic parameters.

From FIGS. 6A-6C, it can be seen that there are errors between the joint positioning results according to human morphological parameters and the joint positions calculated according to the kinematic parameters, so the positioning analysis results are compensated.

Firstly, translation of the positioning analysis results of the 22 joints is carried out. Select a standard joint point of the translation. In this embodiment, seven points are selected as the standard joint points of the translation: the cervicale, the abdomen-pelvic joint (a geometric center of iliospinale anterius and iliospinale posterius), the thoracic vertebrae point, the wrist joints and the ankle joints; calculate the difference between measured coordinates and the positioning coordinates of the standard joint point to determine the translation amount, the translation amount is determined according to a least square method; translating all positioned joints according to the translation amount.

Then, the joints on the upper limb and the lower limb after translation are rotated respectively. Select the standard joint point of the rotation, in this embodiment, the thoracic vertebrae point after translation is selected as the standard joint point of the rotation; calculate the upper limb rotation amount of the wrist joint after translation and the wrist joint before translation relative to the height axis passing through the standard joint point of the rotation; rotate joints on the upper limb after the translation according to the upper limb rotation amount; calculate the lower limb rotation amount of the ankle joint after translation and the ankle joint before translation relative to the height axis passing through the standard joint point of rotation; rotate joints on the lower limb after translation according to the lower limb rotation amount.

Figure 7:
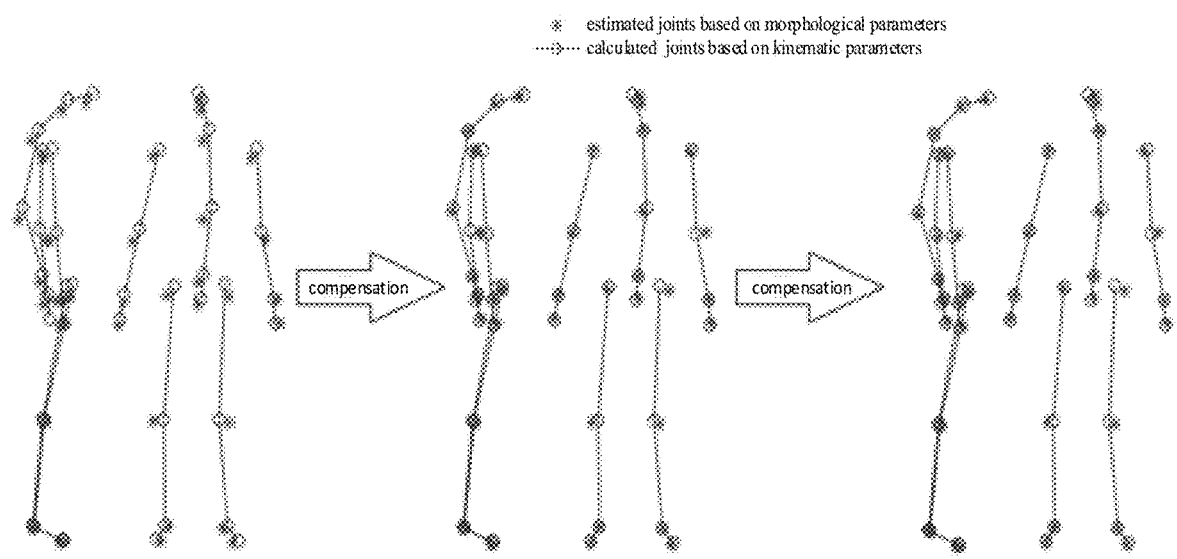
FIG. 7 shows positioning analysis results of subject 7 after compensation in the embodiment shown in FIG. 4 of the positioning analysis method of human functional joint rotation center according to the present invention.

FIG. 7 shows the positioning analysis results of subject 7 after translation and rotation compensation. It can be seen that after translation and rotation, the joint position estimated according to morphological parameters and the joint position calculated according to kinematic parameters are highly overlapped, although there are still errors which are within an acceptable range. This proves the effectiveness and accuracy of the positioning analysis method of human functional joints rotation center provided by the present invention, the positioning analysis method of human functional joint rotation center of the present invention realizes estimating the position of the joint rotation center only according to the human morphological parameters obtained by short 3D scanning, makes the positioning analysis of the joint position get rid of the complex kinematic analysis, and makes a estimation speed of joint position reach a higher value.

Embodiment 4

In this embodiment, influence of each principal component on the joint positioning result is analyzed.

Based on averages of principal components of morphological parameters of 30 subjects, within a fluctuation range of positive and negative triple variance, taking a principal component as a single variable, range and limitation of effect of each principal component on the joint rotation center are observed.

Figure 8:
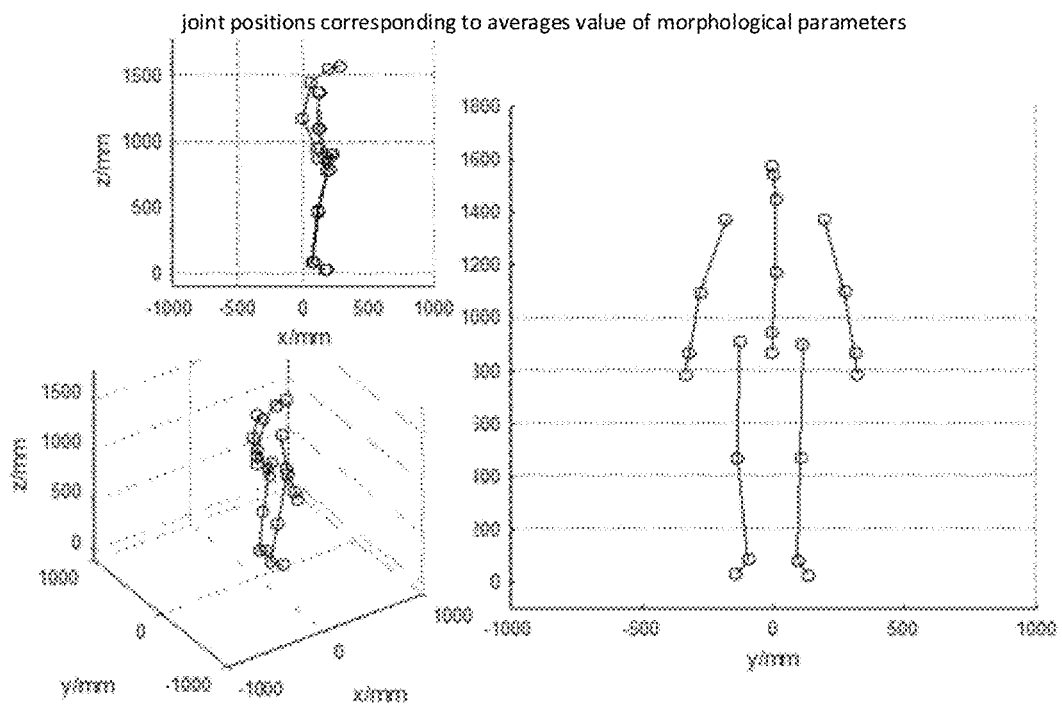
FIG. 8 is a schematic diagram of joint positioning analysis results corresponding to averages value of morphological parameters of the embodiment shown in FIG. 4 of the positioning analysis method of human functional joint rotation center according to the present invention.
Figure 9A:
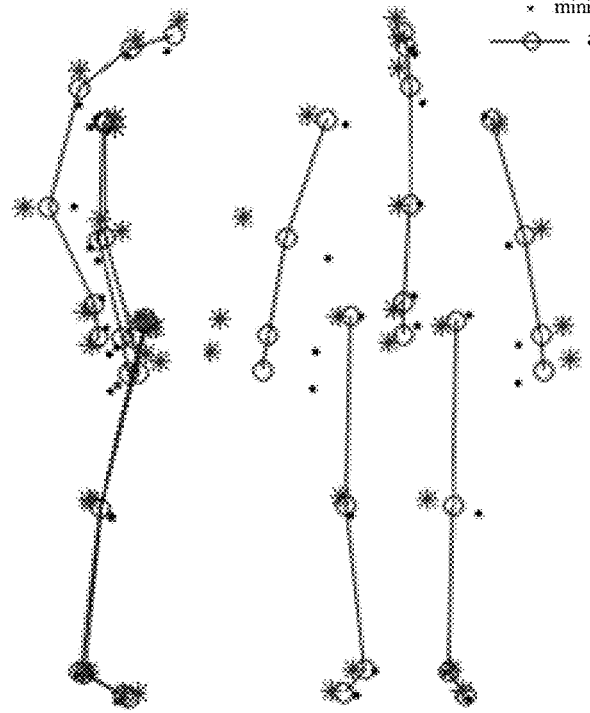
FIGS. 9A-9L are schematic diagrams of range and limitation of effect of each principal component on the joint positioning analysis results of the embodiment shown in FIG. 4 of the positioning analysis method of human functional joint rotation center according to the present invention.
Figure 9B:
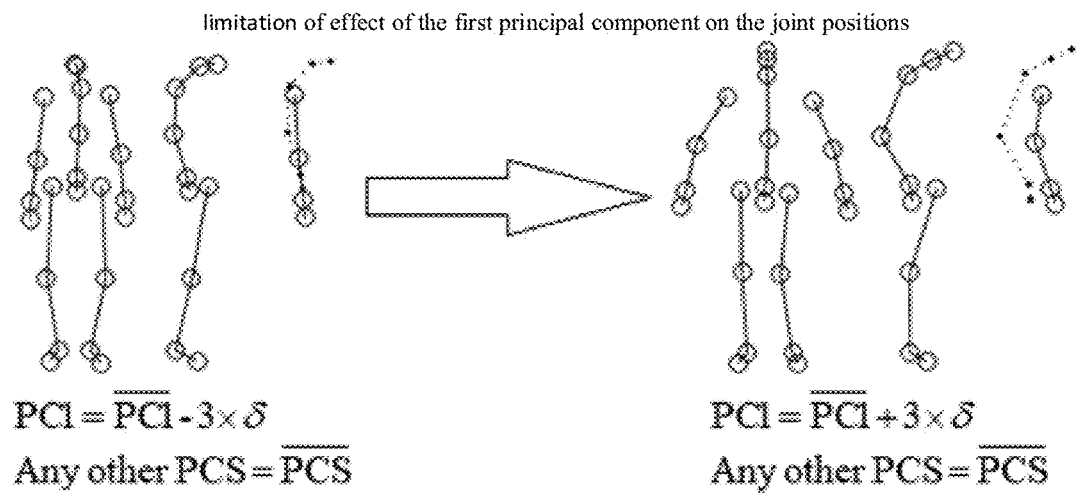
Figure 9C:
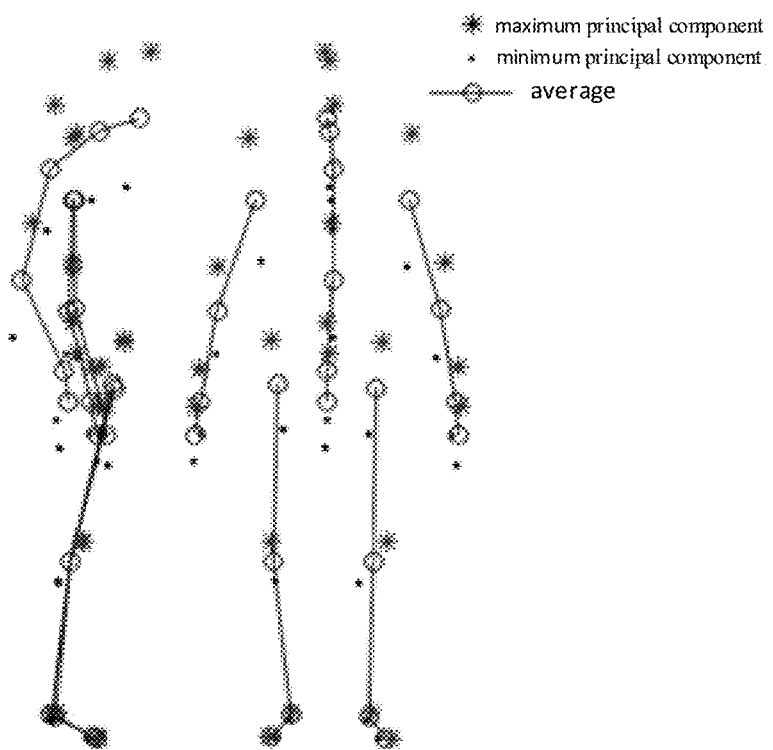
Figure 9D:
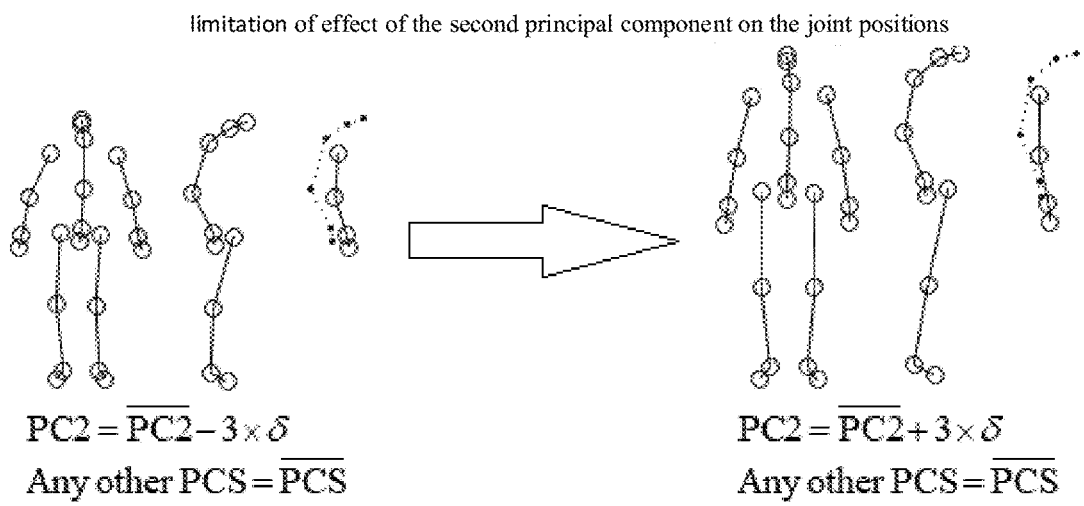
Figure 9E:
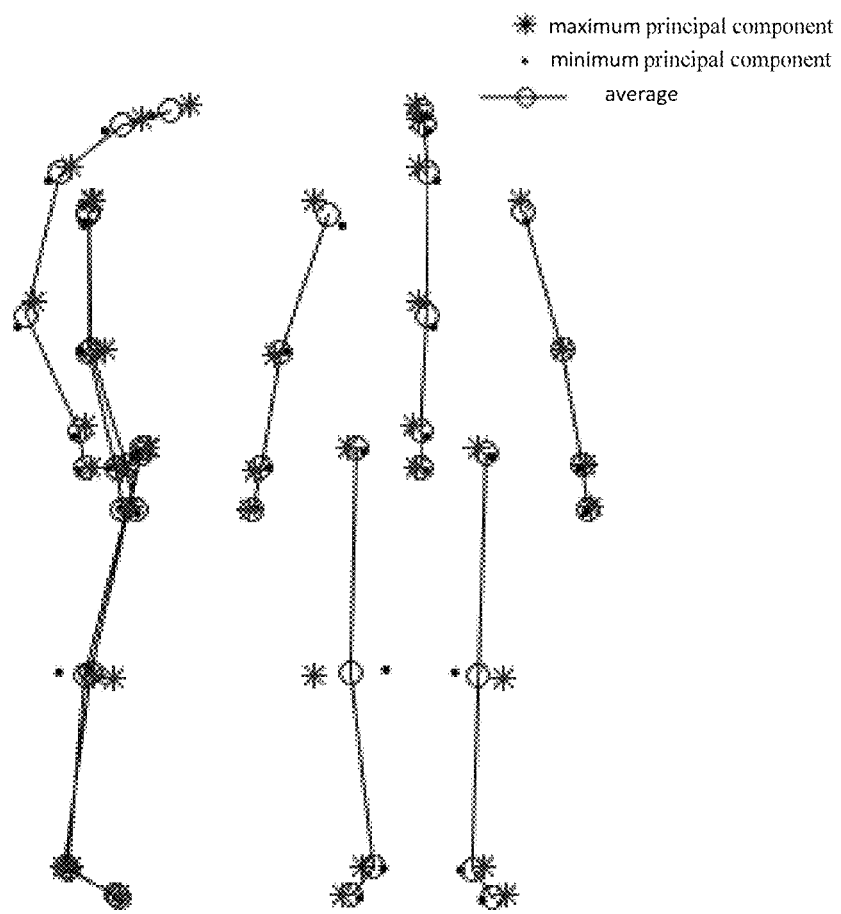
Figure 9F:
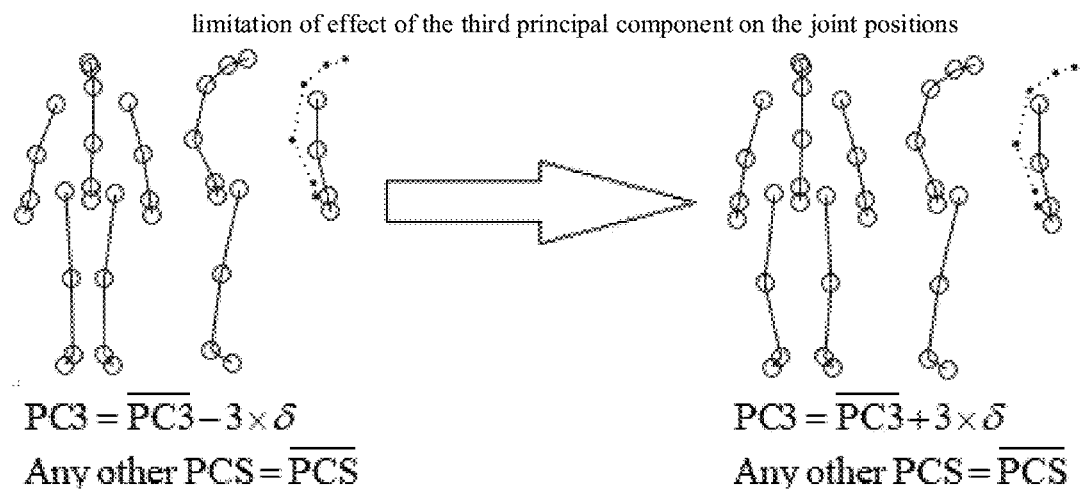
Figure 9G:
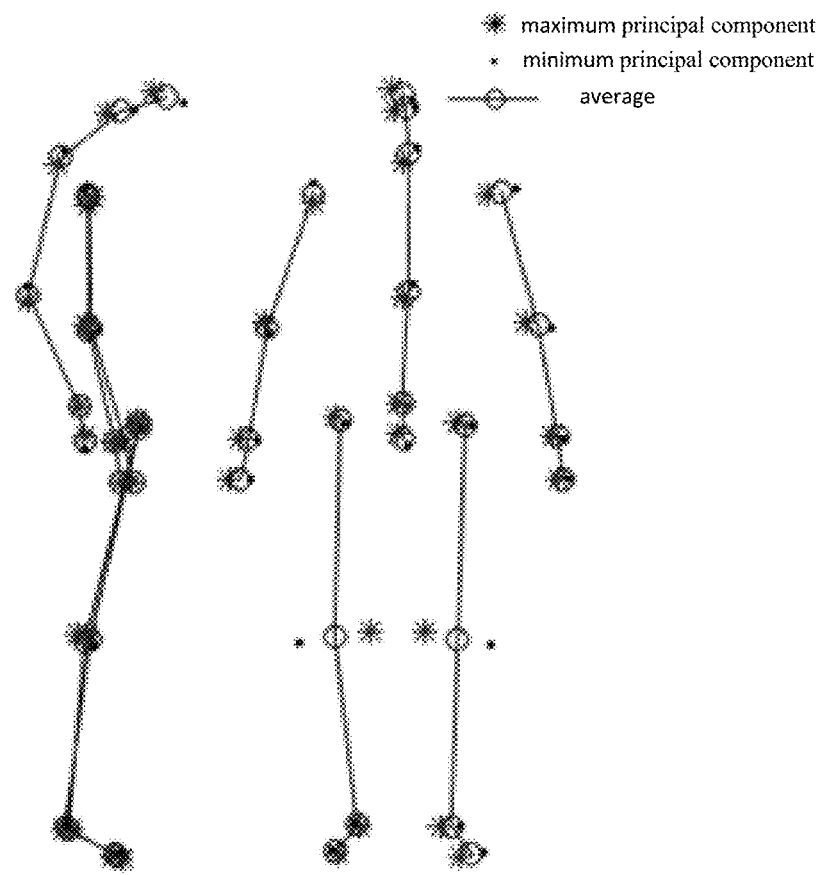
Figure 9H:
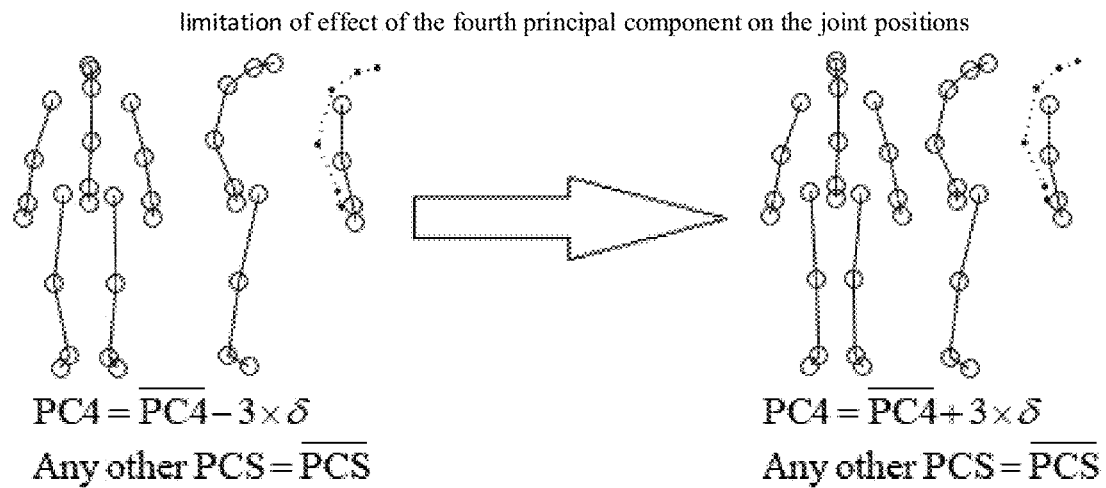
Figure 9I:
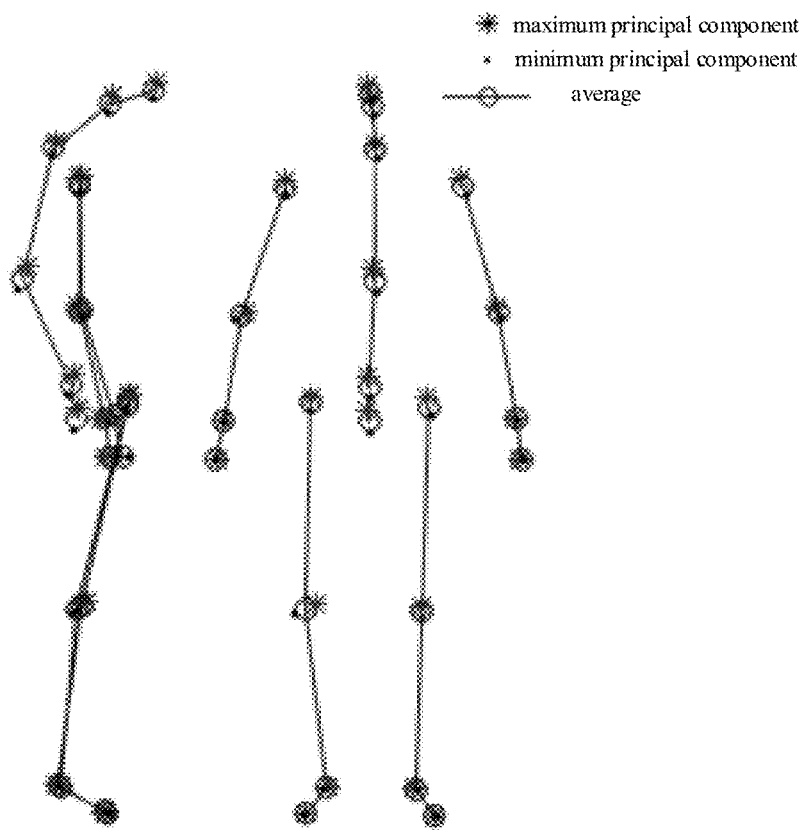
Figure 9J:
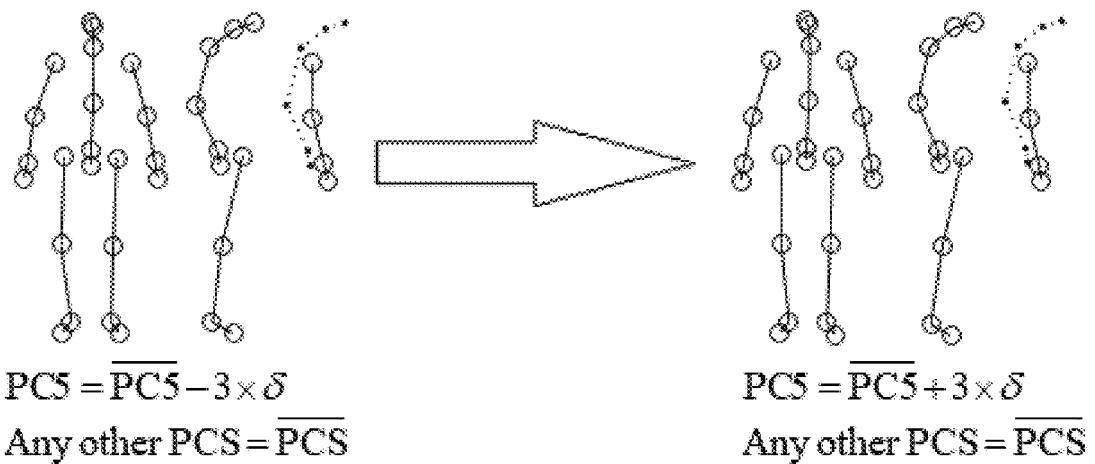
Figure 9K:
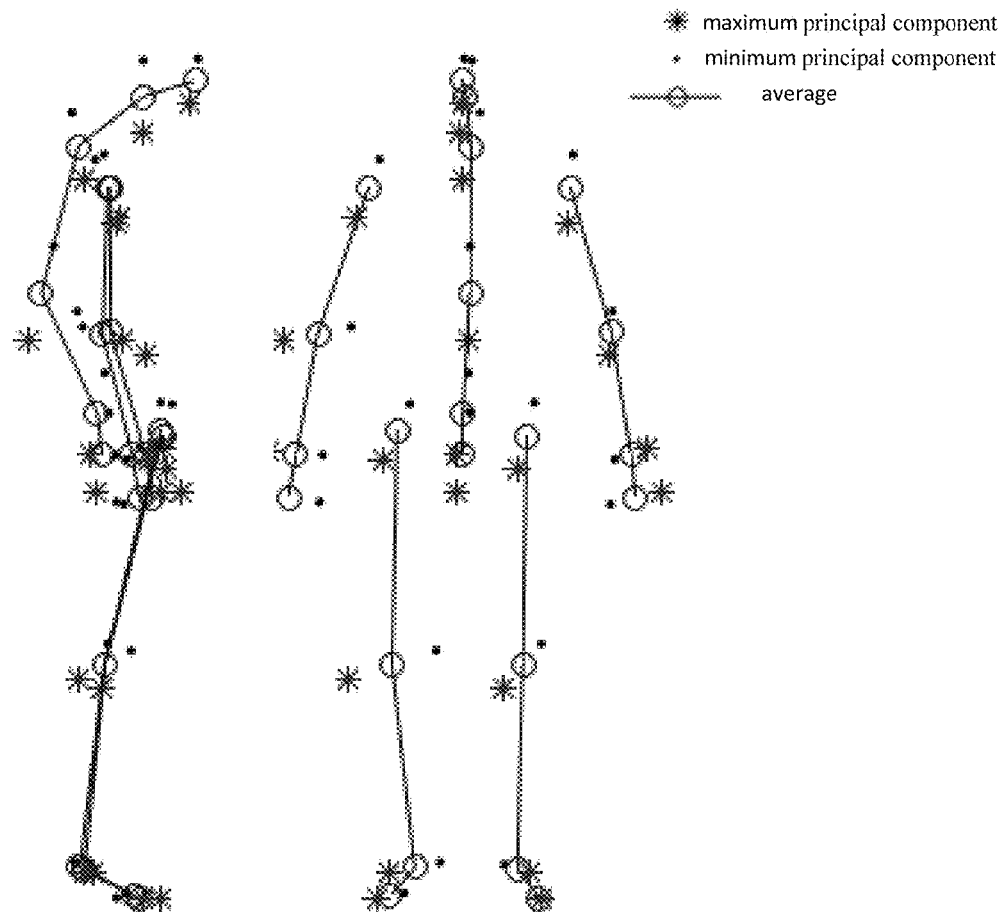
Figure 9L:
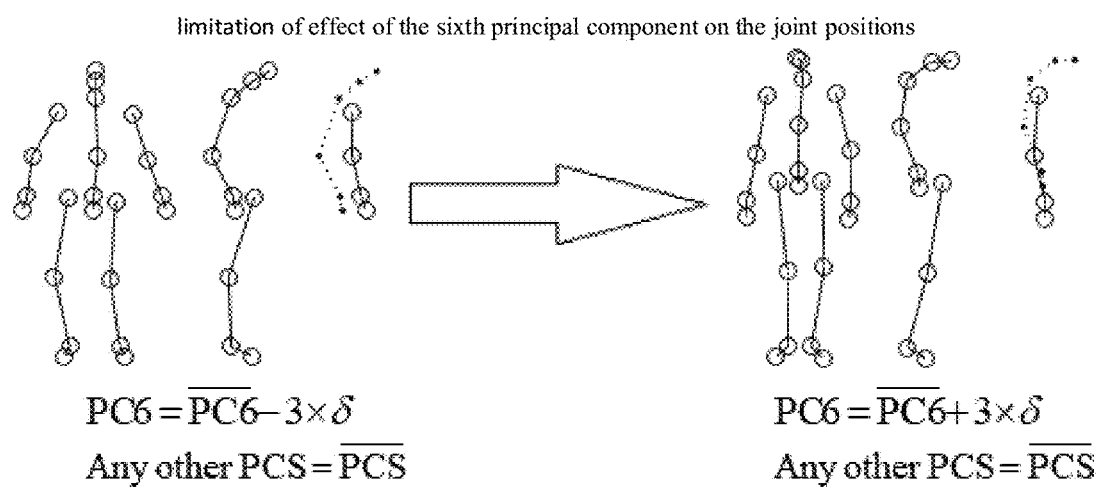

FIG. 8 is a schematic diagram of joint positioning analysis results corresponding to averages value of morphological parameters.

FIGS. 9A-9L are schematic diagrams of range and limitation of effect of each principal component on the joint positioning analysis results with each principal component being taken as a single variable in turn.

From FIG. 8 and FIGS. 9A-9L, it can be seen that the first principal component represents the width and the circumference of an upper body, and the subjects with larger first principal component have wider and thicker upper body; the second principal component represents the height of the human body; the third principal component is not highly representative of the human body, but according to the items with factor load coefficient greater than 0.4 in table 3, i.e. distance to wall and total head length, it is speculated that this principal component represents a forward tilt angle of the human body in standing, and the standing posture of persons with larger third principal component inclines more forward; the fourth principal component represents a distance between human knees, and only the medial malleolus height is with a factor load coefficient greater than 0.4, it is speculated that the medial malleolus height is related to a foot rotation which affects the knee; the fifth principal component represents a ratio of limbs to body, and the subjects with larger fifth principal component have longer arms; the sixth principal component represents a ratio of human lower limbs to height, put simply, the hip of the subjects with larger sixth principal component is higher than that of the human body with a same or similar height.

Embodiment 5

In this embodiment, when establishing the fitting relationship between human morphological parameters and human joint position, the principal component analysis is not performed for human morphological parameters, and the fitting relationship is directly established. In this way, although the amount of data calculation is relatively large, the estimation accuracy is higher.

It should be noted that the above embodiments are only used to illustrate the technical solutions of the present invention, but not to limit them; although the foregoing embodiments have been described in detail, those skilled in the art should understand that they can modify recorded technical solutions in the foregoing embodiments or equivalently replaced some or all of the technical features, and these replacements do not cause the essence of the corresponding technical solutions to deviate from the scope of the technical solutions of the present invention.

What is claimed is:

1. A detecting method of a human shoulder joint rotation center of a person, wherein the method comprises:
   step 1a: in a continuous motion of the person, abstracting from the motion of the person based on a 3D scanning of the person the human shoulder joint rotation center of the person as a center of a flexible ball, and the flexible ball meets constraint conditions:
   A. distances between three mark points M1, M2 and M3 on a relevant body section of the shoulder joint rotation center are within a specified range, and the three mark points M1, M2 and M3 are points on a spherical surface of the flexible ball to account for skin deformations of said person during said motion;
   B. distances between the center of the flexible ball and the three mark points M1, M2, M3 on the flexible ball vary within a specific range during said motion rather than an exact value;
   C. a motion trajectory of the shoulder joint rotation center is continuous;
   step 1b: at any moment during a test, determining position coordinates of the center of the flexible ball at a present moment according to position coordinates of the three mark points M1, M2 and M3 on the relevant body section of the shoulder joint rotation center, and then in the continuous motion, determining position information of the center of the flexible ball according to position information of the three mark points M1, M2 and M3, and then the motion trajectory of the shoulder joint rotation center is obtained in the continuous motion;
   a specific process of the step 1b is:
   (1) in a positioning motion, converting the position coordinates of the three mark points M1, M2 and M3 in an absolute coordinate system to a position coordinates in a chest coordinate system;
   (2) in the chest coordinate system, fixing coordinates of the shoulder joint rotation center, so a relationship of distance from centers $P_{Ot}^L$ and $P_{Ot+dt}^L$ of a mark point set in the chest coordinate system to the shoulder joint rotation center $P_{Jt}$ and $P_{Jt+dt}$ is expressed as:

$$|P_{Jt} - P_{Ot}^L| = |P_{Jt+dt} - P_{Ot+dt}^L| \qquad (1)$$

$$P_{Jt} = P_{Jt+dt} = P_{Ot}^L + R_t^L \tilde{P}_J^L \qquad (2)$$

wherein, $R_t^L$ is a rotation matrix of an upper arm, $\tilde{P}_J^L$ is a constant vector from an origin to the shoulder joint rotation center in a marking point coordinate system of the upper arm, $\tilde{P}_J^L$ is converted to coordinates in the chest coordinate system by the rotation matrix $R_t^L$, $P_{Jt}$ is coordinates of the shoulder joint rotation center in the chest coordinate system at time t, $P_{Jt+dt}$ is coordinates of the shoulder joint rotation center in the chest coordinate system at time t+dt, dt is less than or equal to 1 second;
   (3) obtaining a linear equation by combining equation (1) and equation (2):

$$A_t \tilde{P}_J^L = B_t \qquad (3)$$

wherein $A_t = 2(P_{Ot}^L - P_{Ot+dt}^L)^T R_t^L$, $B_t = -((P_{Ot}^L)^T P_{Ot}^L - (P_{Ot+dt}^L)^T P_{Ot+dt}^L)$;
in the positioning motion from capture time 0 to time T, an integral of equation (3) is:

$$|A_0 \ldots A_t \ldots A_T|^T \tilde{P}_J^L = |B_0 \ldots B_t \ldots B_T|^T \qquad (4)$$

wherein $$A_t = 2 \begin{bmatrix} r_{1xt} - r_{1xt+dt} & r_{1yt} - r_{1yt+dt} & r_{1zt} - r_{1zt+dt} \\ \vdots & \vdots & \vdots \\ r_{nxt} - r_{nxt+dt} & r_{nyt} - r_{nyt+dt} & r_{nzt} - r_{nzt+dt} \end{bmatrix},$$

$$B_t = \begin{bmatrix} r_{1xt}^2 + r_{1yt}^2 + r_{1zt}^2 - r_{1xt+dt}^2 - r_{1yt+dt}^2 - r_{1zt+dt}^2 \\ \vdots \\ r_{nxt}^2 + r_{nyt}^2 + r_{nzt}^2 - r_{nxt+dt}^2 - r_{nyt+dt}^2 - r_{nzt+dt}^2 \end{bmatrix},$$

$r_{1xt}$ represents an X coordinate value of the mark point M1 at time t in the upper arm coordinate system, $r_{1yt}$ represents a Y coordinate value of the mark point M1 at time t in the upper arm coordinate system, $r_{1zt}$ represents a Z coordinate value of the mark point M1 at time t in the upper arm coordinate system, $r_{nxt}$ represents an X coordinate value of the mark point Mn at time t in the upper arm coordinate system, $r_{nyt}$ represents a Y coordinate value of the mark point Mn at time tin the upper arm coordinate system, $r_{nzt}$ represents a Z coordinate value of the mark point Mn at time tin the upper arm coordinate system, and n=3;

(4) according to equation ④, determining $\tilde{P}_J^L$ by a least square method;

(5) converting $\tilde{P}_J^L$ to the position coordinates in the chest coordinate system by the rotation matrix, and then converting to position coordinates in the absolute coordinate system, and then the detection result of the shoulder joint rotation center is obtained.

2. The detecting method of the human shoulder joint rotation center according to the claim 1, wherein, for a shoulder joint rotation center detection, the relevant body section is a human upper arm, wherein the three mark points M1, M2 and M3 are located on the human upper arm.

3. A positioning analysis method of a human shoulder joint rotation center, comprising step 2a: obtaining morphological parameters of a human body by said 3D scanning;

step 2b: according to a fitting relationship between the morphological parameters of the human body and human joints, positioning and analyzing the human joints;

step 2c: compensating positioning analysis results of the human joints;

determining the fitting relationship between the morphological parameters of the human body and the human joints described in the step 2b comprises:

step 2b1: determining position coordinates of the human joints under a standing posture of the human body;

step 2b2: determining N principal components of the morphological parameters of the human body by carrying out a principal component analysis of the morphological parameters of the human body;

step 2b3: fitting the N principal components of the morphological parameters of the human body with the position coordinates of the human joints under the standing posture of the human body determined in the step 2b1 to obtain the fitting relationship:

$$\begin{cases} FCRix = a_{ix1} \cdot PC1 + a_{ix2} \cdot PC2 + \ldots + a_{ixN} \cdot PCN \\ FCRiy = a_{iy1} \cdot PC1 + a_{iy2} \cdot PC2 + \ldots + a_{iyN} \cdot PCN \\ FCRiz = a_{iz1} \cdot PC1 + a_{iz2} \cdot PC2 + \ldots + a_{izN} \cdot PCN \end{cases}$$

wherein, FCRix, FCRiy and FCRiz represent an x coordinate, a y coordinate and a z coordinate of an ith joint respectively, $a_{ix1}, a_{ix2}, \ldots, a_{ixN}, a_{iy1}, a_{iy2}, \ldots, a_{iyN}, a_{iz1}, a_{iz2}, \ldots, a_{izN}$ are fitting coefficients, PC1, PC2, ..., PCN are the N principal components of the morphological parameters of the human body;

in the step 2b1, position coordinate of a shoulder joint is determined by the detecting method of the human shoulder joint rotation center according to claim 1.

4. The positioning analysis method of the human shoulder joint rotation center, according to the claim 3, wherein, in the step 2c, compensation of the positioning analysis results of the human joints comprises a translation and a rotation, the translation comprises: selecting a first standard joint point of the translation; calculating a difference between measured coordinates and positioning coordinates of the first standard joint point to determine a translation amount; translating all positioned joints according to the translation amount.

5. The positioning analysis method of the human shoulder joint rotation center according to the claim 4, wherein the rotation comprises: selecting a second standard joint point of the rotation; calculating an upper limb rotation amount of a wrist joint after the translation and the wrist joint before the translation relative to a height axis passing through the second standard joint point of the rotation; rotating joints on an upper limb after the translation according to the upper limb rotation amount.

6. The positioning analysis method of the human shoulder joint rotation center according to claim 3, wherein the three mark points M1, M2 and M3 are located on the human upper arm.

* * * * *